(12) United States Patent
Pauluth et al.

(10) Patent No.: US 6,287,650 B1
(45) Date of Patent: Sep. 11, 2001

(54) ORGANOSILICON COMPOUNDS

(75) Inventors: Detlef Pauluth, Ober-Ramstadt; Matthias Bremer, Darmstadt; Edgar Böhm, Taipei, all of (DE); Akio Osabe, Kanagawa Pref. (JP); Gerhard Herget, Ober-Ramstadt; Wolfgang Hechler, Lautertal, both of (DE)

(73) Assignee: Merck Patent Gesellschaft mit (DE)

( * ) Notice: Subject to any disclaimer, the term of this patent is extended or adjusted under 35 U.S.C. 154(b) by 0 days.

(21) Appl. No.: 09/186,281

(22) Filed: Nov. 5, 1998

(30) Foreign Application Priority Data

Nov. 5, 1997 (DE) .............................. 197 48 808

(51) Int. Cl.$^7$ .................................... C09K 19/30
(52) U.S. Cl. ................. 428/1.23; 427/387; 252/299.63; 556/479
(58) Field of Search ....................... 252/299.63; 556/479; 428/1.23; 427/387

(56) References Cited

U.S. PATENT DOCUMENTS

| | | | |
|---|---|---|---|
| 5,292,452 | * 3/1994 | Buchecker et al. | ............. 252/299.61 |
| 5,965,761 | * 10/1999 | Buchhecker et al. | ................. 556/440 |
| 5,993,690 | * 11/1999 | Kondo et al. | ....................... 252/299.6 |

* cited by examiner

*Primary Examiner*—Margaret G. Moore
(74) *Attorney, Agent, or Firm*—Millen, White, Zelano & Branigan, P.C.

(57) ABSTRACT

$$R^1—(A^1)_m—Z^1—A^2—(Z^2—A^3)_n—W—SiX_aY_bZ_c \quad I$$

in which
$R^1, A^1, A^2, A^3, Z^1, R^1, Z^2, W, X, Y, Z, m, n, a, b$ and $c$ are as defined below, can be used to produce homeotropic alignment of liquid-crystalline phases on surfaces.

10 Claims, No Drawings

ORGANOSILICON COMPOUNDS

The invention relates to novel organosilicon compounds of the formula I $$R^1-(A^1)_m-Z^1-A^2-(Z^2-A^3)_n-W-SiX_aY_bZ_c \qquad I$$

in which
- $R^1$ is a chiral or achiral alkyl group having up to 10 carbon atoms, in which, in addition, one or two non-adjacent $CH_2$ groups may be replaced by —O— atoms, or is F, Cl or a halogenated alkyl, alkoxy, alkenyl or alkenyloxy radical having 1 to 3 carbon atoms
- $A^1$, $A^2$ and $A^3$ are each, independently of one another,
  - a) a 1,4-cyclohexylene radical, in which, in addition, one or two non-adjacent $CH_2$ groups may be replaced by —O— and/or —S—,
  - b) a 1,4-cyclohexenylene radical, or
  - c) a 1,4-phenylene radical, in which, in addition, one or more CH groups may be replaced by N atoms, where the radicals a), b) and c) may be substituted by one or two fluorine atoms,
- $Z^1$ and $Z^2$ are each —$CH_2CH_2$—, —CO—O—, —$C_2H_4$—, —$(CH_2)_4$—, —$CH_2CH=CHCH_2$—, —$CH_2$—O—, —O—$CH_2$—, —O—$CF_2$—, —$CF_2$—O—, —CH=CH—, —C≡C— or a single bond,
- m is 0 or 1,
- n is 0, 1 or 2 where m+n is $\geq 1$,
- W is a straight-chain or branched alkylene group having up to 10 carbon atoms, in which, in addition, one or two non-adjacent $CH_2$ groups may be replaced by —CHF— and/or —CH($CF_3$)—,
- X, Y and Z are each, independently of one another, OCN, CN, R', OR', H or Cl, where at least one of the substituents X, Y and Z is not H,
- R' is an alkyl group having 1 to 15 carbon atoms, in which, in addition, one or more non-adjacent $CH_2$ groups may be replaced by —O—, —CO— and/or —CH=CH—, and
- a, b and c are 0, 1, 2 or 3, where a+b+c=3.

The compounds of the formula I are excellently suitable for the homeotropic alignment of liquid-crystalline phases on surfaces, for example glass plates, which may also be coated, as used in the production of electro-optical display elements. The alignment of liquid-crystalline phases oriented in this way can be modified by an external electric field owing to their negative dielectric anisotropy. They are suitable for use in displays operated on the principle of deformation of aligned phases (Appl. Phys. Lett. 19, 391 (1971)), the principle of dynamic scattering (Proc. IEE 56, 1162 (1968)) or the guest-host principle (Mol. Cryst. Liq. Cryst. 63, 19 (1981)).

It was hitherto technically quite difficult to produce a uniform and stable homeotropic alignment of liquid-crystalline phases. For example, the liquid-crystalline phase used has been doped with surface-active substances, such as lecithins, long-chain aliphatic amines, quaternary ammonium or phosphonium salts or carboxylatochromium complexes (Appl. Phys. Lett., 268 (1975)). Also common was coating of glass surfaces with said substances before introduction of the liquid-crystalline phase. However, the uniformity and stability of the resultant homeotropic alignment of liquid-crystalline phases are unsatisfactory.

German Patent Applications P 33 31 515 and P 36 01 742 disclose trialkanoyloxysilanes for producing a homeotropic alignment of liquid-crystalline phases on surfaces. However, these compounds have a number of disadvantages. For example, their preparation from acid anhydrides and trichlorosilanes is frequently accompanied by the formation of dark-brown byproducts, which can be separated from the desired trialkanoyloxysilane only with difficulty. Products contaminated in this way are not suitable for surface treatment, since they reduce the optical transparency of the substrate material. Furthermore, hydrolysis of the trialkanoyloxy compounds on the substrate surface by the process indicated in P 33 31 515 frequently results only in low-molecular-weight hydrolysis products, which are volatile with the steam used and thus do not contribute to the modification of the treated surface, which results in complete or only partial surface alignment of liquid-crystalline phases applied. Furthermore, it has been found in practice that the known alignment materials very frequently do not exhibit uniform perpendicular alignment, which means that complex processes, such as inclined vapour deposition, are still—as also in most known organosilicon compounds—necessary in addition to the alignment material.

There is, therefore, a demand for stable, novel organosilicon compounds which can be used to achieve uniform tilt without additional process steps having to be carried out.

The invention therefore had the object of enabling better, in particular more uniform and more stable homeotropic alignment of liquid-crystalline phases on surfaces. This object has been achieved by the provision of the compounds of the formula I.

The invention thus relates to the compounds of the formula I and to a process for their preparation, characterized in that an unsaturated compound of the formula II $$R^1-(A^1)_m-Z^1-A^2-(Z^2-A^3)_n-W-CH=CH_2 \qquad II$$

is reacted with a silane H—$SiX_aY_bZ_c$, in which $R^1$, $A^1$, $A^2$, $A^3$, $Z^1$, $Z^2$, m, n, X, Y, Z, W, a, b and c are as defined above, or in that a halide of the formula III $$R^1-(A^1)_m-Z^1-A^2-(Z^2-A^3)_n-W-Hal \qquad (III)$$

is reacted with a silane H—$SiX_aY_bZ_c$, in which $R^1$, $A^1$, $A^2$, $A^3$, $Z^1$, $Z^2$, m, n, X, Y, Z, W, a, b and c are as defined above, and Hal is Cl, Br or I.

The invention furthermore relates to the use of the compounds of the formula I as components of liquid-crystalline dielectrics for electro-optical display elements, and to their use for producing homeotropic alignment of liquid-crystalline phases on surfaces. The compounds of the formula I also enable the surface tension to be matched to the liquid-crystalline mixture in the display. Furthermore, the compounds according to the invention have an antistatic action and are therefore highly suitable as adhesion promoters to the polymer films in the display. The silicon compounds may additionally be used to build up an ion-barrier layer.

The invention also relates to the use of compounds of the formula I in printing processes for producing homeotropic alignment of liquid-crystalline phases on surfaces.

The invention furthermore relates to liquid-crystalline dielectrics containing at least one compound of the formula I, and to electro-optical display elements containing dielectrics of this type and/or containing surfaces which have been treated with a compound of the formula I.

Above and below, $R^1$, $A^1$, $A^2$, $A^3$, $Z^1$, $Z^2$, n, X, Y, Z, W, R', a, b and c are as defined above, unless expressly stated otherwise.

According to the definitions of the various groups, the compounds of the formula I embrace those of the subformulae Ia to If:

| | |
|---|---|
| $R^1$-$A^1$-$A^2$-W-$SiX_aY_bZ_c$ | Ia |
| $R^1$-$A^1$-$Z^1$-$A^2$-W-$SiX_aY_bZ_c$ | Ib |
| $R^1$-$A^1$-$A^2$-$A^2$-W-$SiX_aY_bZ_c$ | Ic |
| $R^1$-$A^1$-$Z^1$-$A^2$-$A^3$-W-$SiX_aY_bZ_c$ | Id |
| $R^1$-$A^1$-$Z^1$-$A^2$-$Z^2$-$A^3$-W-$SiX_aY_bZ_c$ | Ie |

Compounds of the formulae Ia, Ic and Ie are particularly preferred.

Above and below, PheF is 1,4-phenylene which is substituted by fluorine in the ortho-position to $R^1$, and PheFF is 1,4-phenylene which is disubstituted by fluorine in each ortho-position to $R^1$. Cy denotes a 1,4-cyclohexylene group.

The compounds of the subformula Ia embrace the preferred compounds of the subformulae Iaa and Iai:

| | |
|---|---|
| $R^1$-PheF-Phe-W-$SiX_aY_bZ_c$ | Iaa |
| $R^1$-PheF-Cy-W-$SiX_aY_bZ_c$ | Iab |
| $R^1$-PheFF-Phe-W-$SiX_aY_bZ_c$ | Iac |
| $R^1$-PheFF-Cy-W-$SiX_aY_bZ_c$ | Iad |
| F-PheF-Phe-W-$SiX_aY_bZ_c$ | Iae |
| F-PheF-Cy-W-$SiX_aY_bZ_c$ | Iaf |
| $R^1$-Phe-Phe-W-$SiX_aY_bZ_c$ | Iag |
| $R^1$-Phe-Cy-W-$SiX_aY_bZ_c$ | Iah |
| $R^1$-Cy-Cy-W-$SiX_aY_bZ_c$ | Iai |

Particular preference is given to the compounds of the formulae Iaa, Iab, Iae, Iaf, Iag and Iai.

The compounds of the subformula Ib embrace the preferred compounds of the subformulae Iba to Ibh:

| | |
|---|---|
| $R^1$-PheF-$Z^1$-Phe-W-$SiX_aY_bZ_c$ | Iba |
| $R^1$-PheF-$Z^1$-Cy-W-$SiX_aY_bZ_c$ | Ibb |
| $R^1$-PheFF-$Z^1$-Phe-W-$SiX_aY_bZ_c$ | Ibc |
| $R^1$-PheFF-$Z^1$-Cy-W-$SiX_aY_bZ_c$ | Ibd |
| F-PheF-$Z^1$-Phe-W-$SiX_aY_bZ_c$ | Ibe |
| F-PheF-$Z^1$-Cy-W-$SiX_aY_bZ_c$ | Ibf |
| $R^1$-Phe-$Z^1$-Phe-W-$SiX_aY_bZ_c$ | Ibg |
| $R^1$-Phe-$Z^1$-Cy-W-$SiX_aY_bZ_c$ | Ibh |

The compounds of the subformula Ic embrace the preferred compounds of the subformulae Ica to Icp:

| | |
|---|---|
| $R^1$-PheF-Phe-Phe-W-$SiX_aY_bZ_c$ | Ica |
| $R^1$-PheF-Phe-Cy-W-$SiX_aY_bZ_c$ | Icb |
| $R^1$-PheF-Cy-Phe-W-$SiX_aY_bZ_c$ | Icc |
| $R^1$-PheF-Cy-Cy-W-$SiX_aY_bZ_c$ | Icd |
| $R^1$-PheFF-Phe-Phe-W-$SiX_aY_bZ_c$ | Ice |
| $R^1$-PheFF-Phe-Cy-W-$SiX_aY_bZ_c$ | Icf |
| $R^1$-PheFF-Cy-Phe-W-$SiX_aY_bZ_c$ | Icg |
| $R^1$-PheFF-Cy-Cy-W-$SiX_aY_bZ_c$ | Ich |
| F-PheF-Phe-Phe-W-$SiX_aY_bZ_c$ | Ici |
| F-PheF-Phe#y-W-$SiX_aY_bZ_c$ | Icj |
| F-PheF-Cy-Phe-W-$SiX_aY_bZ_c$ | Ick |
| F-PheF-Cy-Cy-W-$SiX_aY_bZ_c$ | Icl |
| $R^1$-Phe-Phe-Phe-W-$SiX_aY_bZ_c$ | Icm |
| $R^1$-Phe-Phe-Cy-W-$SiX_aY_bZ_c$ | Icn |
| $R^1$-Phe-Cy-Phe-W-$SiX_aY_bZ_c$ | Ico |
| $R^1$-Phe-Cy-Cy-W-$SiX_aY_bZ_c$ | Icp |

Of these, the compounds of the subformulae Icc, Ica, Icp and Ich are particularly preferred.

The compounds of the subformula Id embrace the preferred compounds of the subformulae Ida to Idl:

| | |
|---|---|
| $R^1$-PheF-$Z^1$-Phe-Phe-W-$SiX_aY_bZ_c$ | Ida |
| $R^1$-PheF-$Z^1$-Phe-Cy-W-$SiX_aY_bZ_c$ | Idb |
| $R^1$-PheF-$Z^1$-Cy-Phe-W-$SiX_aY_bZ_c$ | Idc |
| $R^1$-PheF-$Z^1$-Cy-Cy-W-$SiX_aY_bZ_c$ | Idd |
| $R^1$-PheFF-$Z^1$-Phe-Phe-W-$SiX_aY_bZ_c$ | Ide |
| $R^1$-PheFF-$Z^1$-Phe-Cy-W-$SiX_aY_bZ_c$ | Idf |
| $R^1$-PheFF-$Z^1$-Cy-Phe-W-$SiX_aY_bZ_c$ | Idg |
| $R^1$-PheFF-$Z^1$-Cy-Cy-W-$SiX_aY_bZ_c$ | Idh |
| $R^1$-Phe-$Z^1$-Phe-Phe-W-$SiX_aY_bZ_c$ | Idi |
| $R^1$-Phe-$Z^1$-Phe-Cy-W-$SiX_aY_bZ_c$ | Idj |
| $R^1$-Phe-$Z^1$-Cy-Phe-W-$SiX_aY_bZ_c$ | Idk |
| $R^1$-Phe-$Z^1$-Cy-Cy-W-$SiX_aY_bZ_c$ | Idl |

The compounds of the subformula Ie embrace the preferred compounds of the subformulae Iea to Iel:

| | |
|---|---|
| $R^1$-PheF-Phe-$Z^2$-Phe-W-$SiX_aY_bZ_c$ | Iea |
| $R^1$-PheF-Phe-$Z^2$-Cy-W-$SiX_aY_bZ_c$ | Ieb |
| $R^1$-PheF-Cy-$Z^2$Phe-W-$SiX_aY_bZ_c$ | Iec |
| $R^1$-PheF-Cy-$Z^2$-Cy-W-$SiX_aY_bZ_c$ | Ied |
| $R^1$-PheFF-Phe-$Z^2$-Phe-W-$SiX_aY_bZ_c$ | Iee |
| $R^1$-PheFF-Phe-$Z^2$-Cy-W-$SiX_aY_bZ_c$ | Ief |
| $R^1$-PheFF-Cy-$Z^2$-Phe-W-$SiX_aY_bZ_c$ | Ieg |
| $R^1$-PheFF-Cy-$Z^2$-Cy-W-$SiX_aY_bZ_c$ | Ieh |
| $R^1$-Phe-Phe-$Z^2$-Phe-W-$SiX_aY_bZ_c$ | Iei |
| $R^1$-Phe-Phe-$Z^2$-Cy-W-$SiX_aY_bZ_c$ | Iej |
| $R^1$-Phe-Cy-$Z^2$-Phe-W-$SiX_aY_bZ_c$ | Iek |
| $R^1$-Phe-Cy-$Z^2$-Cy-W-$SiX_aY_bZ_c$ | Iel |

The compounds of the subformula If embrace the preferred compounds of the subformulae Ifa to Ifl:

| | |
|---|---|
| $R^1$-PheF-$Z^1$-Phe-$Z^2$-Phe-W-$SiX_aY_bZ_c$ | Ifa |
| $R^1$-PheF-$Z^1$-Phe-$Z^2$-Cy-W-$SiX_aY_bZ_c$ | Ifb |
| $R^1$-PheF-$Z^1$-Cy-$Z^2$-Phe-W-$SiX_aY_bZ_c$ | Ifc |
| $R^1$-PheF-$Z^1$-Cy-$Z^2$-Cy-W-$SiX_aY_bZ_c$ | Ifd |
| $R^1$-PheFF-$Z^1$-Phe-$Z^2$-Phe-W-$SiX_aY_bZ_c$ | Ife |
| $R^1$-PheFF-$Z^1$-Phe-$Z^2$-Cy-W-$SiX_aY_bZ_c$ | Iff |
| $R^1$-PheFF-$Z^1$-Cy-$Z^2$Phe-$SiX_aY_bZ_c$ | Ifg |
| $R^1$-PheFF-$Z^1$-Cy-$Z^2$-Cy-W-$SiX_aY_bZ_c$ | Ifh |
| $R^1$-Phe-$Z^1$-Phe-$Z^2$-Phe-W-$SiX_aY_bZ_c$ | Ifi |
| $R^1$-Phe-$Z^1$-Phe-$Z^2$Cy-W-$SiX_aY_bZ_c$ | Ifj |
| $R^1$-Phe-$Z^1$-Cy-$Z^2$-Phe-W-$SiX_aY_bZ_c$ | Ifk |
| $R^1$-Phe-$Z^1$-Cy-$Z^2$-Cy-W-$SiX_aY_bZ_c$ | Ifl |

In the compounds of the formulae above and below, X, Y and Z are preferably identical (a=b=c=1) and are preferably —OR', in which R' is preferably an alkyl group having 1–8 carbon atoms, particularly preferably 1–5 carbon atoms, very particularly preferably 1—3 carbon atoms. Furthermore, one or more non-adjacent $CH_2$ groups in R' may also be replaced by —O—, —CO— and/or —CH=CH—. X, Y and Z are furthermore also chlorine.

Accordingly, OR' is preferably methoxy, ethoxy, propoxy, furthermore butoxy, pentoxy, hexyloxy, heptyloxy, octyloxy, nonyloxy, decyloxy or 2-oxapropyl (=methoxymethyl).

2-Oxabutyl (=ethoxymethyl) or 3-oxabutyl (=3—methoxyethyl), 2-, 3-, or 4-oxapentyl, 2-, 3-, 4- or 5-oxahexyl, 2-, 3-, 4-, 5-, 6-oxaheptyl, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl, 1,3-dioxabutyl (=methoxymethoxy), 1,3-, 1,4- or 2,4-dioxapentyl, 1,3-, 1,4-, 1,5-, 2,4-, 2,5- or 3,5-dioxahexyl, or 1,3-, 1,4-, 1,5-, 1,6-, 2,4-, 2,5-, 2,6-, 3,5-, 3,6- or 4,6-dioxaheptyl.

Very particularly preferred compounds are those of the formulae above and below in which X, Y and Z are methoxy, ethoxy, propoxy, isopropoxy or 1-methyl-3-oxabut-1-enyloxy.

X, Y and Z are furthermore also R', where R' has the preferred meanings already described elsewhere, and accordingly are preferably methyl, ethyl, propyl, butyl, pentyl, hexyl, heptyl, octyl, nonyl, decyl, 2-oxapropyl (=methoxymethyl), 2-oxabutyl (=ethoxymethyl) or 3-oxabutyl (=3-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl, 1,3-dioxabutyl (=methoxymethoxy), 1,3-, 1,4- or 2,4-dioxapentyl, 1,3-, 1,4-, 1,5-, 2,4-, 2,5- or 3,5-dioxahexyl, or 1,3-, 1,4-, 1,5-, 1,6-, 2,4-, 2,5-, 2,6-, 3,5-, 3,6- or 4,6-dioxaheptyl.

In the compounds of the formulae above and below, $R^1$ is preferably fluorine or a chiral alkyl group having 1 to 10 carbon atoms, furthermore a chiral alkoxy group or another chiral oxaalkyl group. $R^1$ is furthermore also Cl, $OCF_3$, $OCHF_2$, $OCH=CF_2$, $OCF=CF_2$, $OCF=CF_2$, $OCH_2CF_3$, $OCH_2CHF_2$, $OC_2F_5$ or $OCHFCF_3$.

The chiral groups of $R^1$ generally contain not more than one chain branch. Preferred branched radicals $R^1$ are isopropyl, 2-butyl (=1-methylpropyl), isobutyl (=2-methylpropyl), 2-methylbutyl, isopentyl (=3-methylbutyl); $R^1$ may furthermore be 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 1-methylhexyloxy, 1-methylheptyloxy, 2-ethylhexyloxy, 2-oxa-3-methylbutyl or 3-oxa-4-methylpentyl.

If the groups $A^2$ and/or $A^3$ are 1,4-disubstituted cyclohexylene groups, the substituents can be in the cis- or trans-position. The compounds having a trans-configuration are preferred.

$Z^1$ and $Z^2$ are preferably, independently of one another, a single bond, furthermore preferably a —$CH_2CH_2$— or —CO—O— group. They are furthermore also a —$CH_2$—O—, —CH=CH— or —C≡C— group.

The parameter n can be 0, 1 or 2 and is preferably 1.

In the compounds of the formulae above and below, W is preferably a straight-chain alkylene group having 1–10 carbon atoms, particularly preferably having 2–6 carbon atoms, and accordingly is, in particular, —$C_2H_4$—, —$(CH_2)_3$—, —$(CH_2)_4$—, —$(CH_2)_5$—, or —$(CH_2)_6$—, furthermore also —$C_2H_4$—$CH_2$—, —$(CH_2)_7$—, $(CH_2)_8$—, —$(CH_2)_9$— or $(CH_2)_{10}$—.

Furthermore, one or two non-adjacent $CH_2$ groups in W can also be replaced by —CHF— or —CH($CF_3$)— having a centre of chirality. Preference is given to groups such as, for example, —$(CH_2)_2$—CHF—$CH_2$—, —$(CH_2)_2$—CH($CF_3$)—$CH_2$— or —$(CH_2)$—CHF—$(CH_2)_3$—.

Furthermore, the alkylene group in W may also be branched and have a centre of chirality. Branched groups of this type generally contain not more than one chain branch. Preferred branched groups are, for example, isopropylene, 2-butylene, isobutylene, 2-methylbutylene, isopentylene, 2-methylpentylene, 2-ethylhexylene or 2-propylpentylene.

The various lists of particularly preferred meanings for the individual parameters are to be taken as merely illustrative and in no way have a limiting character.

Compounds of the formula I containing optically active carbon atoms cover the racemates and the corresponding optically active enantiomers, and mixtures thereof.

Some particularly preferred organosilicon compounds of the formula I are mentioned below ($L^1$ and $L^2$ are H or F):

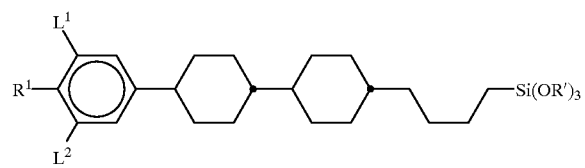

I1

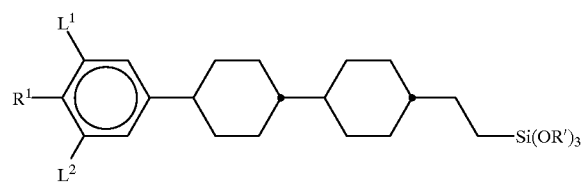

I2

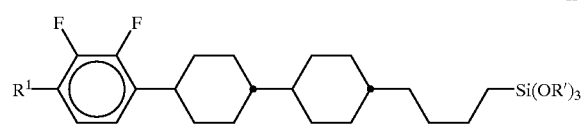

I3

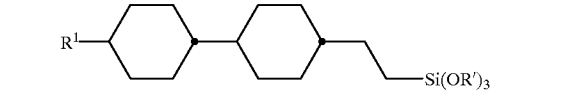

I4

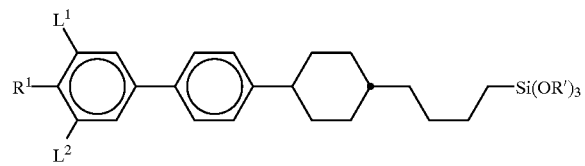

I5

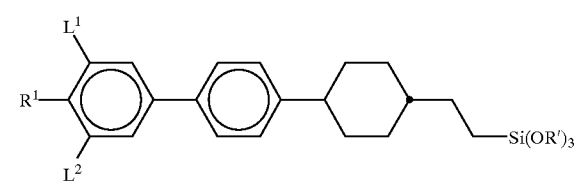

I6

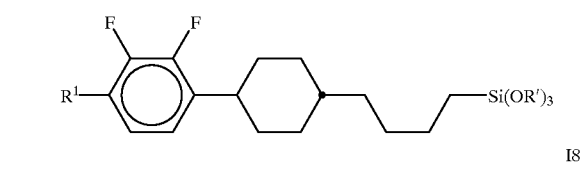

I7

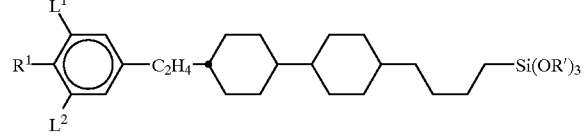

I8

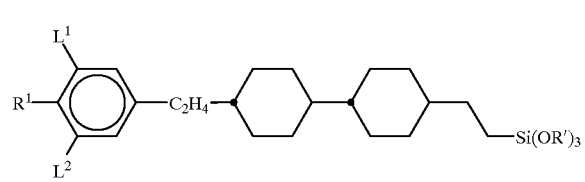

I9

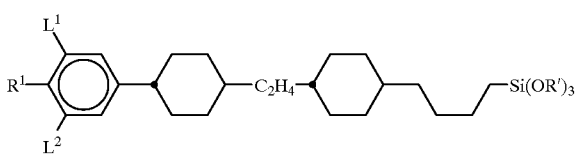
I10

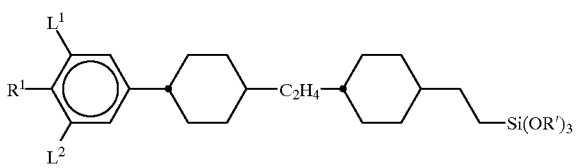
I11

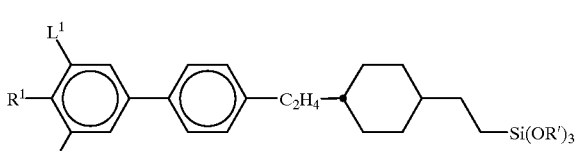
I12

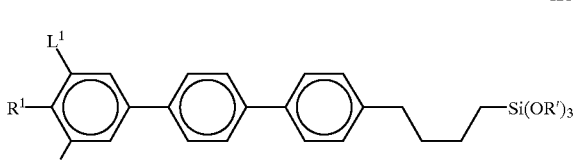
I13

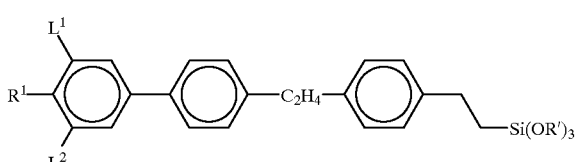
I14

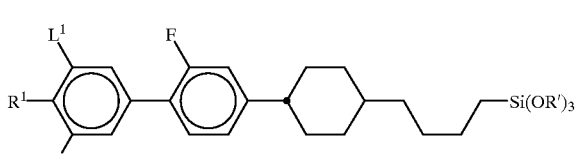
I15

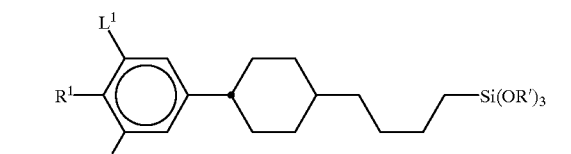
I16

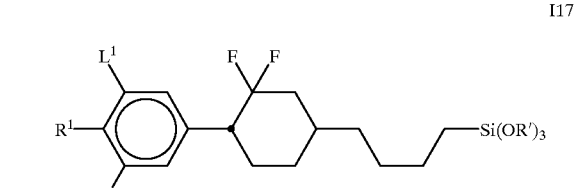
I17

$R^1$ in subformulae I1–I17 is preferably fluorine or straight-chain alkyl having up to 6 carbon atoms. R' is preferably methyl or ethyl. In the compounds of the formulae I1 to I17, the 1,4-phenylene rings and the cyclohexane rings may also be substituted by one or more fluorine atoms. Particular preference is given to 3,5-difluoro-1,4-phenylene, 2-fluoro-1,4-phenylene, 3-fluoro-1,4-phenylene and furthermore 2,3-difluorophenylene.

The compounds of the formula I can be prepared by methods known per se, as described in the literature (for example in the standard works such as Houben-Weyl, Methoden der Organischen Chemie [Methods of Organic Chemistry], Vol. XIII, 5, Georg-Thieme-Verlag, Stuttgart), to be precise under reaction conditions which are known and suitable for said reactions. Use can also be made here of variants which are known per se, but are not mentioned here in greater detail.

Compounds of the formula I can be prepared for example, as follows:

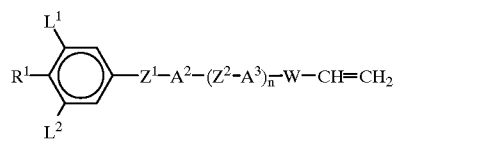
II

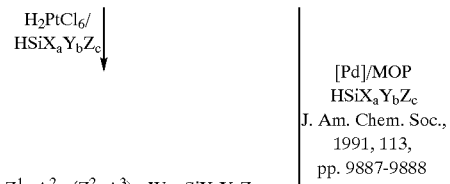

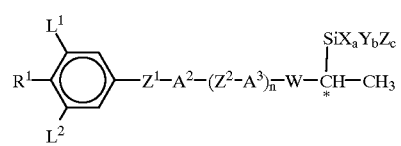

MOP = chiral monodentate phosphine ligand

The silanes of the formula H—$SiX_aY_bZ_c$ are known or can be prepared by known methods, as described, for example, in the above literature.

The addition reaction of the silanes H—$SiX_aY_dZ_c$ onto the unsaturated alkenes of the formula II is advantageously carried out in the presence of an inert solvent, for example a halogenated hydrocarbon, such as dichloromethane, and at temperatures between 0° C. and about 100° C., advantageously at the boiling point. Silane is advantageously employed in excess. The addition of a noble-metal catalyst, for example a solution of $H_2PtCl_6$, in isopropanol is advantageous. The reaction can also be accelerated by addition of peroxides, such as diacetyl peroxide, and/or by irradiation with light. Further suitable catalysts are, for example, also platinum complexes with dicyclopentadiene or rhodium and nickel complexes.

Chiral compounds can be prepared using, for example, a catalyst prepared in situ from a palladium complex, for example $[PdCl(\pi-C_3H_5)]_2$, and a monodentate chiral binaphthylphosphine compound, as described in J. Am. Chem. Soc. 1991, 113, 9887.

For use in printing processes, where the use of polar solvents is advisable, the reaction of the halosilanes of the formula I can be carried out in an excess of the relevant alcohol. Resultant solutions of organosilicon compounds of the formula I can then, if desired after removal of the salt formed during the reaction from the added organic base, be used directly for the surface coating.

The compounds of the formula I can be used directly for coating the surfaces to be treated. Particularly suitable for coating are oxidic surfaces, for example those of metal oxides, semi-metal oxides or nonmetal oxides, but in particular glass surfaces.

The coating is advantageously carried out by wetting the precleaned surfaces with an approximately 0.1 to 1% solution of a compound of the formula I in a solvent, such as, for example, a halogenated hydrocarbon, such as dichloromethane or 1,1,1-trichloroethane, or lower alcohols, and evaporating the solvent in the air. Heating or steam aftertreatment of the surface modified in this way, as in the compound claimed in DE-A33 31 515, is generally unnecessary in the case of the compounds of the formula I. A uniform, high-molecular-weight film which is capable of homeotropically aligning liquid-crystalline phases is formed. For uniform alignment, additional shear between two glass plates at elevated temperature may be necessary. In order to simplify handling of compounds of the formula I, they can be dissolved in a suitable inert solvent, such as, for example, 1,1,1-trichloroethane, immediately after their preparation and after removal of volatile reaction components by distillation, and stored in a bottle sealed with a septum stopper. By means of a syringe, only the amount required in each case is removed from the storage bottle, so that the remainder of the solution remains protected against hydrolysis through atmospheric moisture.

The compounds of formula I thus represent an effective means of producing a homeotropic alignment of liquid-crystalline phases on surfaces.

Another application of the compounds of the formula I is use for the preparation of liquid-crystalline pigments, for example through three-dimensional crosslinking of silanols prepared from the compounds of the formula I. Application of the silanols in the liquid state to a smooth substrate produces a film, which is hardened, removed from the substrate and comminuted to give platelet-like particles. Before further processing or use in surface coatings, in particular automotive paints, printing inks and plastics, excessively large and small pigments are removed by a particle-size-selective separation process. The usable pigments have a particle diameter in the order of from 5 to 200 μm, preferably from 5 to 100 μm, in particular from 5 to 60 μm. When a medium provided with the pigments according to the invention is applied to a surface, the platelet-like pigments automatically line up parallel to the surface owing to flow processes in the base coat or in the printing ink.

However, one or more compounds of the formula I can also be added as dopants to liquid-crystalline dielectrics, these dielectrics containing from about 0.01 to 1% by weight, preferably from about 0.05 to 0.5% by weight, of compounds of the formula I.

The dielectrics according to the invention consist of from 2 to 25, preferably from 3 to 15, components, including at least one compound of the formula I. The other constituents are preferably selected from nematic or nematogenic substances, in particular known substances from the classes of the azoxybenzenes, benzylideneanilines, biphenyls, terphenyls, phenyl or cyclohexyl benzoates, phenyl or cyclohexyl cyclohexanecarboxylates, phenylcyclohexanes, cyclohexylbiphenyls, cyclohexylcyclohexanes, cyclohexylnaphthalenes, 1,4-biscyclohexylbenzenes, 4,4'-bis-cyclohexylbiphenyls, phenyl- or cyclohexylpyrimidines, phenyl- or cyclohexyldioxanes, phenyl- or cyclohexyldithianes, 1,2-biscyclohexylethanes, 1,2-bisphenylethanes, 1-cyclohexyl-2-phenylethanes, optionally halogenated stilbenes, benzyl phenyl ethers, tolans and substituted cinnamic acids.

The most important constituents of such liquid-crystalline dielectrics of the suitable compounds may be characterized by the formula V, $$R'—L—G—E—R''\qquad V$$

in which L and E are each a carbocyclic or heterocyclic ring system from the group formed by 1,4-disubstituted benzene and cyclohexane rings, 4,4'-disubstituted biphenyl, phenylcyclohexane and cyclohexylcyclohexane systems, 2,5-disubstituted pyrimidine and 1,3-dioxane rings, 2,6-disubstituted naphthalene, di- and tetrahydronaphthalene, quinazoline and tetrahydroquinazoline,

| G is | —CH=CH— | —N(O)=N— |
|---|---|---|
| | —CH=CY— | —CH=N(O)— |
| | —C≡C— | —CH$_2$CH$_2$— |
| | —CO—O— | —CH$_2$—O— |
| | —CO—S— | —CH$_2$—S— |
| | —CH=N— | —COO-Phe-COO— | or a C—C single bond, Y is halogen, preferably chlorine, or —CN, and R' and R'' are alkyl, alkoxy, alkanoyloxy or alkoxycarbonyloxy having up to 18, preferably up to 8, carbon atoms, or one of these radicals is alternatively CN, NCS, NC, NO$_2$, OCF$_3$, CF$_3$, F, Cl or Br. The benzene and cyclohexane rings may also be substituted by F, Cl, —CN or —CH$_3$.

In most of these compounds, R' and R'' are different from one another, one of these radicals usually being an alkyl or alkoxy group. However, other variants of the proposed substituents are common. Many such substances and also mixtures thereof are commercially available.

The dielectrics according to the invention are prepared in a manner conventional per se. In general, the components are dissolved in one another, advantageously at elevated temperature.

By means of suitable additives, the liquid-crystalline dielectrics according to the invention can be modified in such a way that they can be used in all types of liquid-crystal display elements disclosed hitherto.

Additives of this type are known to the person skilled in the art and are described in detail in the literature. For example, conductive salts, for example ethyldimethyldodecylammonium 4-hexyloxybenzoate, tetrabutylammonium tetraphenylborate or complex salts of crown ethers (cf., for example, I. Haller et al., Mol. Cryst. Liq., Volume 24, pages 249–258 (1973)) can be added to improve the conductivity, dichroic dyes can be added to prepare coloured guest/host systems or substances can be added to modify the dielectric anisotropy, the viscosity and/or the alignment of the nematic phases. Such substances are described, for example, in DE-A 22 09 127, 22 40 864, 23 21 632, 23 38 281, 24 50 088, 26 37 430, 28 53 728 and 29 02 177.

The examples below are intended to illustrate the invention without representing a limitation. m.p.=melting point, cl. p.=clearing point. Above and below, percentage data are per cent by weight; all temperatures are given in degrees Celsius.

EXAMPLES

Example 1

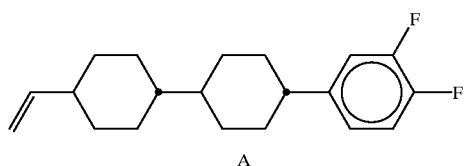

A

↓

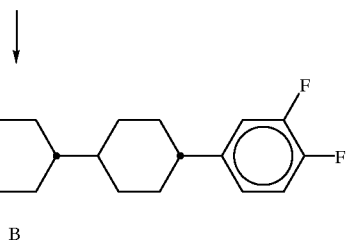

B

Under an $N_2$ atmosphere, 50 mmol of trimethoxysilane and 10 drops of a solution of 164 mg of $H_2PtCl_6$ in 10 ml of isopropanol are added slowly at room temperature to a solution of 5 mmol of A in 15 ml of dichloromethane. The mixture is stirred overnight, and the solvent and the excess trimethoxysilane are then removed under reduced pressure, firstly at room temperature and then at 35–40° C. The resultant crude product is used for the surface treatment as a 0.1 to 1% solution in dichloromethane.

NMR ($CDCl_3$; 200 MHz): δ=2.44 [benzyl-H]; δ=3.60 [Si($OCH_3$)$_3$]; δ=7.05 [arom.]

The following compounds of the formula

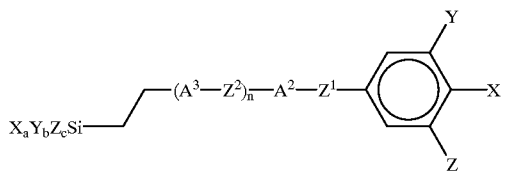

are prepared analogously:

| $X_aY_bZ_c$ | —(A³—Z²)ₙ—A²—Z¹— | X | Y | Z |
|---|---|---|---|---|
| (OCH₃)₃ | cyclohexyl-cyclohexyl | F | H | H |
| (OCH₃)₃ | cyclohexyl-cyclohexyl | F | F | F |
| (OC₂H₅)₃ | cyclohexyl-cyclohexyl | F | H | H |
| (OC₂H₅)₃ | cyclohexyl-cyclohexyl | F | F | H |
| (OC₂H₅)₃ | cyclohexyl-cyclohexyl | F | F | F |
| (OCH₃)₃ | cyclohexyl-phenyl | F | H | H |
| (OCH₃)₃ | cyclohexyl-phenyl | F | F | H |
| (OCH₃)₃ | cyclohexyl-phenyl | F | F | F |
| (OCH₃)₃ | cyclohexyl-phenyl(F) | F | H | H |
| (OCH₃)₃ | cyclohexyl-phenyl(F) | F | F | H |
| (OCH₃)₃ | cyclohexyl-phenyl(F) | F | F | F |
| (OC₂H₅)₃ | cyclohexyl-phenyl | F | H | H |
| (OC₂H₅)₃ | cyclohexyl-phenyl | F | F | H |
| (OC₂H₅)₃ | cyclohexyl-phenyl | F | F | F |
| (OCH₃)₃ | cyclohexyl | F | H | H |
| (OCH₃)₃ | cyclohexyl | F | F | H |

-continued

| $X_aY_bZ_c$ | $—(A^3—Z^2)_n—A^2—Z^1—$ | X | Y | Z |
|---|---|---|---|---|
| (OCH₃)₃ | 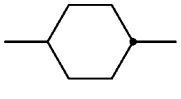 | F | F | F |
| (OC₂H₅)₃ | 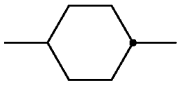 | F | H | H |
| (OC₂H₅)₃ | 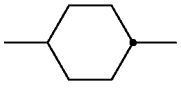 | F | F | H |
| (OC₂H₅)₃ | 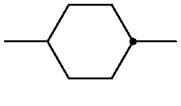 | F | F | F |
| (OCH₃)₃ | 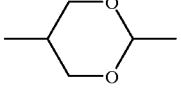 | F | H | H |
| (OCH₃)₃ | 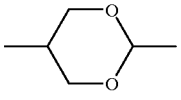 | F | F | H |
| (OCH₃)₃ | 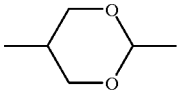 | F | F | F |
| (OC₂H₅)₃ | 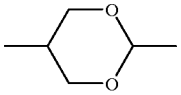 | F | H | H |
| (OC₂H₅)₃ | 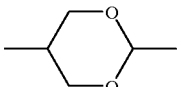 | F | F | H |
| (OC₂H₅)₃ | 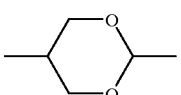 | F | F | F |
| (OCH₃)₃ | 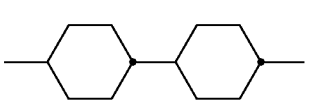 | OCF₃ | H | H |
| (OCH₃)₃ | 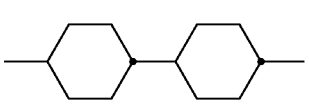 | OCF₃ | F | H |
| (OCH₃)₃ | 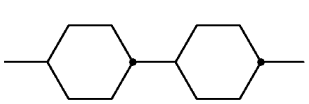 | OCF₃ | F | F |

-continued

| $X_aY_bZ_c$ | $—(A^3—Z^2)_n—A^2—Z^1—$ | X | Y | Z |
|---|---|---|---|---|
| (OC₂H₅)₃ | 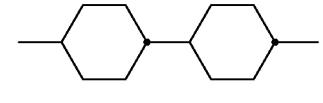 | OCF₃ | H | H |
| (OC₂H₅)₃ | 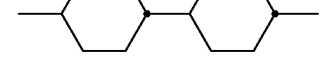 | OCF₃ | F | H |
| (OC₂H₅)₃ | 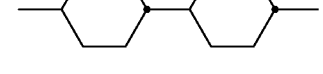 | OCF₃ | F | F |
| (OCH₃)₃ | 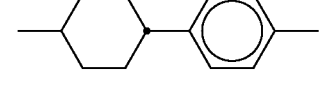 | OCF₃ | H | H |
| (OCH₃)₃ | 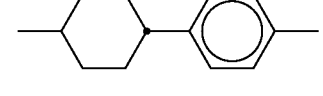 | OCF₃ | F | H |
| (OCH₃)₃ | 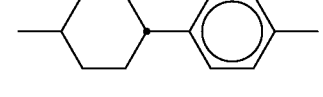 | OCF₃ | F | F |
| (OC₂H₅)₃ | 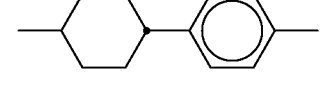 | OCF₃ | H | H |
| (OC₂H₅)₃ | 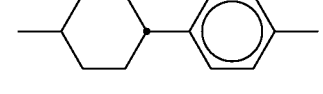 | OCF₃ | F | H |
| (OC₂H₅)₃ | 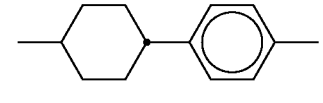 | OCF₃ | F | F |
| (OCH₃)₃ | 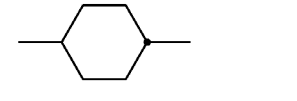 | OCF₃ | H | H |
| (OCH₃)₃ | 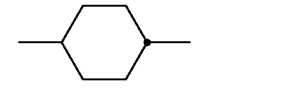 | OCF₃ | F | H |
| (OCH₃)₃ | 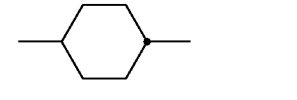 | OCF₃ | F | F |
| (OC₂H₅)₃ | 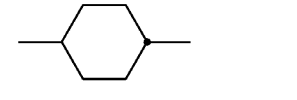 | OCF₃ | H | H |
| (OC₂H₅)₃ |  | OCF₃ | F | H |

| $X_aY_bZ_c$ | $-(A^3-Z^2)_n-A^2-Z^1-$ | X | Y | Z |
|---|---|---|---|---|
| (OC₂H₅)₃ | 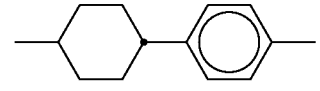 | OCF₃ | F | F |
| (OCH₃)₃ | 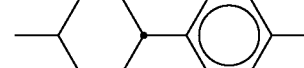 | OCF₃ | H | H |
| (OCH₃)₃ | 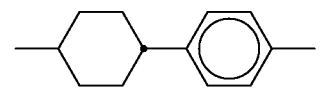 | OCF₃ | F | H |
| (OCH₃)₃ | 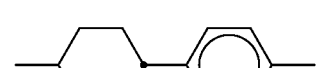 | OCF₃ | F | F |
| (OC₂H₅)₃ | 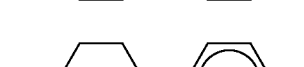 | OCF₃ | H | H |
| (OC₂H₅)₃ | 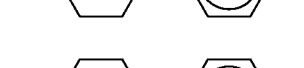 | OCF₃ | F | H |
| (OC₂H₅)₃ | 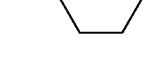 | OCF₃ | F | F |
| (OCH₃)₃ | 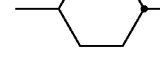 | Cl | H | H |
| (OCH₃)₃ | 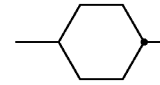 | Cl | F | H |
| (OCH₃)₃ | 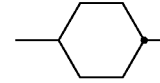 | Cl | F | F |
| (OC₂H₅)₃ | 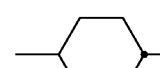 | Cl | H | H |
| (OC₂H₅)₃ | 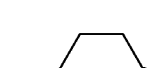 | Cl | F | H |
| (OC₂H₅)₃ | 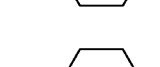 | Cl | F | F |

| $X_aY_bZ_c$ | $-(A^3-Z^2)_n-A^2-Z^1-$ | X | Y | Z |
|---|---|---|---|---|
| (OCH₃)₃ | | Cl | H | H |
| (OCH₃)₃ | | Cl | F | H |
| (OCH₃)₃ | | Cl | F | F |
| (OC₂H₅)₃ | | Cl | H | H |
| (OC₂H₅)₃ | | Cl | F | H |
| (OC₂H₅)₃ | | Cl | F | F |
| (OCH₃)₃ | | Cl | H | H |
| (OCH₃)₃ | | Cl | F | H |
| (OCH₃)₃ | | Cl | F | F |
| (OC₂H₅)₃ | | Cl | H | H |
| (OC₂H₅)₃ | | Cl | F | H |
| (OC₂H₅)₃ | | Cl | F | F |
| (OCH₃)₃ | | Cl | H | H |
| (OCH₃)₃ | | Cl | F | H |

-continued

| $X_aY_bZ_c$ | $-(A^3-Z^2)_n-A^2-Z^1-$ | X | Y | Z |
|---|---|---|---|---|
| (OCH₃)₃ | dioxane-CH | Cl | F | F |
| (OC₂H₅)₃ | dioxane-CH | Cl | H | H |
| (OC₂H₅)₃ | dioxane-CH | Cl | F | H |
| (OC₂H₅)₃ | dioxane-CH | Cl | F | F |
| (OCH₃)₃ | Cy-Cy | CH₃ | H | H |
| (OC₂H₅)₃ | Cy-Cy | CH₃ | H | H |
| (OCH₃)₃ | Cy-Ph | CH₃ | H | H |
| (OC₂H₅)₃ | Cy-Ph | CH₃ | H | H |
| (OCH₃)₃ | Cy | CH₃ | H | H |
| (OC₂H₅)₃ | Cy | CH₃ | H | H |
| Cl₃ | Cy-Cy | F | H | H |
| Cl₃ | Cy-Cy | F | F | H |
| Cl₃ | Cy-Cy | F | F | F |
| (C₂H₅)₃ | Cy-Cy | F | H | H |
| (C₂H₅)₃ | Cy-Cy | F | F | H |
| (C₂H₅)₃ | Cy-Cy | F | F | F |
| (CH₃)₃ | Cy-Ph | F | H | H |
| (CH₃)₃ | Cy-Ph | F | F | H |
| (CH₃)₃ | Cy-Ph | F | F | F |
| Cl₃ | Cy-Ph | F | H | H |
| Cl₃ | Cy-Ph | F | F | H |
| Cl₃ | Cy-Ph | F | F | F |
| (CH₃)₃ | Cy | F | H | H |
| (CH₃)₃ | Cy | F | F | H |
| (CH₃)₃ | Cy | F | F | F |
| (C₂H₅)₃ | Cy | F | H | H |
| (C₂H₅)₃ | Cy | F | F | H |

| $X_aY_bZ_c$ | $—(A^3—Z^2)_n—A^2—Z^1—$ | X | Y | Z |
|---|---|---|---|---|
| $(C_2H_5)_3$ | cyclohexyl | F | F | F |
| $Cl_3$ | dioxane | F | H | H |
| $Cl_3$ | dioxane | F | F | H |
| $Cl_3$ | dioxane | F | F | F |
| $(C_2H_5)_3$ | dioxane | F | H | H |
| $(C_2H_5)_3$ | dioxane | F | F | H |
| $(C_2H_5)_3$ | dioxane | F | F | F |

Example 2

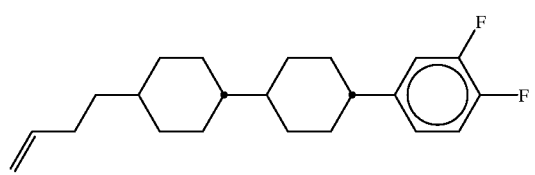

↓ C

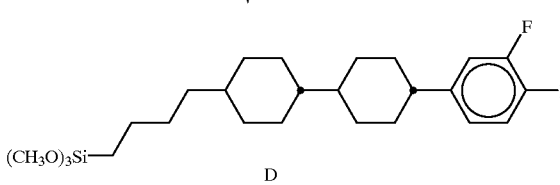

D

Under a nitrogen atmosphere, 45 mmol of trimethoxysilane and 9 drops of a solution of 164 mg of $H_2PtCl_6$ in 10 ml of isopropanol are added slowly at room temperature to a solution of 4.5 mmol of C in 15 ml of dichloromethane. The mixture is stirred overnight, and the solvent and the excess trimethoxysilane are then removed under reduced pressure, firstly at room temperature and then at 35–40° C. The crude product is used for the surface treatment as a 0.2% solution in dichloromethane.

NMR (CDCl$_3$; 300 MHz): δ=2.44 [benzyl-H]; δ=3.6 [Si(OCH$_3$)$_3$]; δ=7.1 [arom.]

The following compounds of the formula

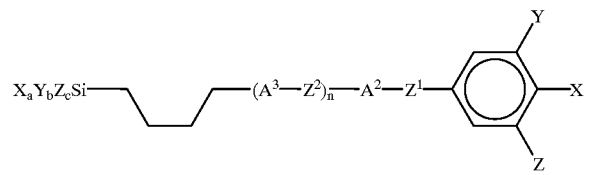

are prepared analogously:

| $X_aY_bZ_c$ | $—(A^3—Z^2)_n—A^2—Z^1$ | X | Y | Z |
|---|---|---|---|---|
| $(OCH_3)_3$ | cyclohexyl-cyclohexyl | F | H | H |
| $(OCH_3)_3$ | cyclohexyl-cyclohexyl | F | F | F |
| $(OC_2H_5)_3$ | cyclohexyl-cyclohexyl | F | H | H |
| $(OC_2H_5)_3$ | cyclohexyl-cyclohexyl | F | F | H |
| $(OC_2H_5)_3$ | cyclohexyl-cyclohexyl | F | F | F |
| $(OCH_3)_3$ | cyclohexyl-phenyl | F | H | H |
| $(OCH_3)_3$ | cyclohexyl-phenyl | F | F | H |
| $(OCH_3)_3$ | cyclohexyl-phenyl | F | F | F |
| $(OC_2H_5)_3$ | cyclohexyl-phenyl | F | H | H |
| $(OC_2H_5)_3$ | cyclohexyl-phenyl | F | F | H |

| $X_aY_bZ_c$ | —(A³—Z²)ₙ—A²—Z¹ | X | Y | Z |
|---|---|---|---|---|
| (OC₂H₅)₃ | 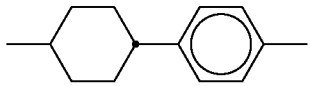 | F | F | F |
| (OC₂H₅)₃ |  | F | H | H |
| (OC₂H₅)₃ |  | F | F | H |
| (OC₂H₅)₃ |  | F | F | F |
| (OCH₃)₃ | 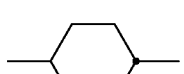 | F | H | H |
| (OCH₃)₃ |  | F | F | H |
| (OCH₃)₃ | 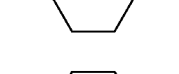 | F | F | F |
| (OC₂H₅)₃ | 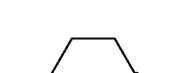 | F | H | H |
| (OC₂H₅)₃ |  | F | F | H |
| (OC₂H₅)₃ | 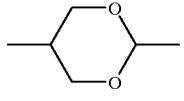 | F | F | F |
| (OCH₃)₃ | 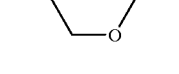 | F | H | H |
| (OCH₃)₃ | 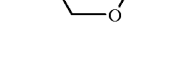 | F | F | H |
| (OCH₃)₃ | 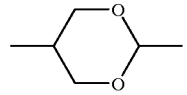 | F | F | F |
| (OC₂H₅)₃ | 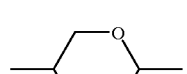 | F | H | H |
| (OC₂H₅)₃ | 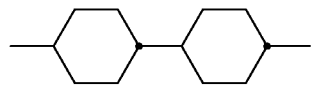 | F | F | H |
| (OC₂H₅)₃ | 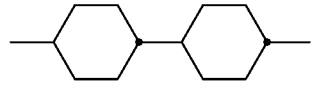 | F | F | F |
| (OCH₃)₃ | 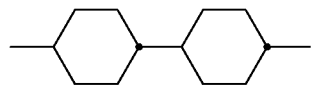 | OCF₃ | H | H |
| (OCH₃)₃ | 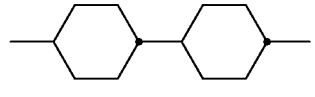 | OCF₃ | F | H |
| (OCH₃)₃ | 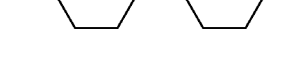 | OCF₃ | F | F |
| (OC₂H₅)₃ |  | OCF₃ | H | H |
| (OC₂H₅)₃ | 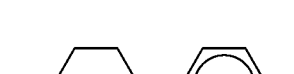 | OCF₃ | F | H |
| (OC₂H₅)₃ | 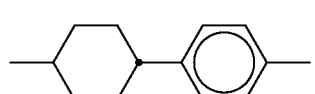 | OCF₃ | F | F |
| (OCH₃)₃ |  | OCF₃ | H | H |
| (OCH₃)₃ |  | OCF₃ | F | H |
| (OCH₃)₃ |  | OCF₃ | F | F |
| (OC₂H₅)₃ |  | OCF₃ | H | H |

-continued

| $X_aY_bZ_c$ | $-(A^3-Z^2)_n-A^2-Z^1$ | X | Y | Z |
|---|---|---|---|---|
| (OC$_2$H$_5$)$_3$ | 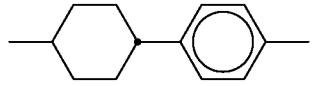 | OCF$_3$ | F | H |
| (OC$_2$H$_5$)$_3$ | 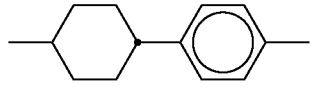 | OCF$_3$ | F | F |
| (OCH$_3$)$_3$ | 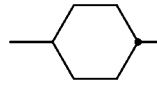 | OCF$_3$ | H | H |
| (OCH$_3$)$_3$ | 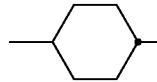 | OCF$_3$ | F | H |
| (OCH$_3$)$_3$ | 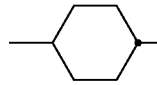 | OCF$_3$ | F | F |
| (OC$_2$H$_5$)$_3$ | 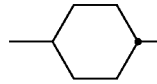 | OCF$_3$ | H | H |
| (OC$_2$H$_5$)$_3$ | 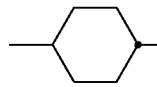 | OCF$_3$ | F | H |
| (OC$_2$H$_5$)$_3$ | 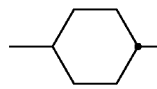 | OCF$_3$ | F | F |
| (OCH$_3$)$_3$ | 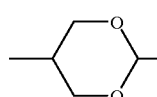 | OCF$_3$ | H | H |
| (OCH$_3$)$_3$ | 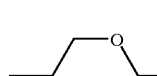 | OCF$_3$ | F | H |
| (OCH$_3$)$_3$ | 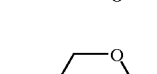 | OCF$_3$ | F | F |
| (OC$_2$H$_5$)$_3$ | 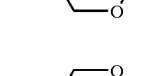 | OCF$_3$ | H | H |
| (OC$_2$H$_5$)$_3$ | 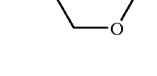 | OCF$_3$ | F | H |

-continued

| $X_aY_bZ_c$ | $-(A^3-Z^2)_n-A^2-Z^1$ | X | Y | Z |
|---|---|---|---|---|
| (OC$_2$H$_5$)$_3$ | 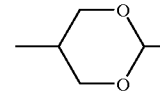 | OCF$_3$ | F | F |
| (OCH$_3$)$_3$ | 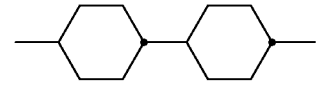 | Cl | H | H |
| (OCH$_3$)$_3$ | 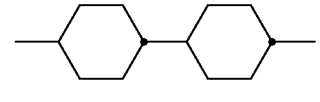 | Cl | F | H |
| (OCH$_3$)$_3$ | 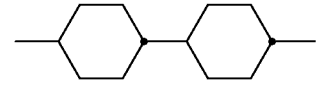 | Cl | F | F |
| (OC$_2$H$_5$)$_3$ | 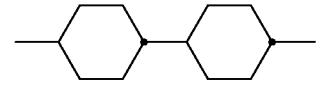 | Cl | H | H |
| (OC$_2$H$_5$)$_3$ | 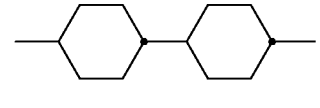 | Cl | F | H |
| (OC$_2$H$_5$)$_3$ | 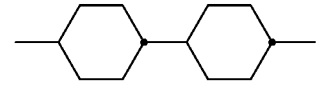 | Cl | F | F |
| (OCH$_3$)$_3$ | 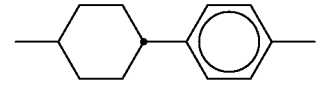 | Cl | H | H |
| (OCH$_3$)$_3$ | 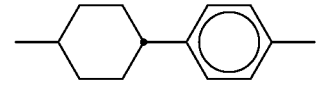 | Cl | F | H |
| (OCH$_3$)$_3$ | 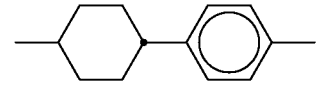 | Cl | F | F |
| (OC$_2$H$_5$)$_3$ | 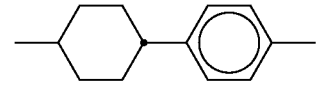 | Cl | H | H |
| (OC$_2$H$_5$)$_3$ | 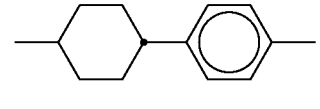 | Cl | F | H |
| (OC$_2$H$_5$)$_3$ | 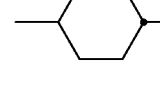 | Cl | F | F |
| (OCH$_3$)$_3$ |  | Cl | H | H |

| $X_aY_bZ_c$ | $-(A^3-Z^2)_n-A^2-Z^1$ | X | Y | Z |
|---|---|---|---|---|
| (OCH$_3$)$_3$ |  | Cl | F | H |
| (OCH$_3$)$_3$ |  | Cl | F | F |
| (OC$_2$H$_5$)$_3$ |  | Cl | H | H |
| (OC$_2$H$_5$)$_3$ |  | Cl | F | H |
| (OC$_2$H$_5$)$_3$ |  | Cl | F | F |
| (OCH$_3$)$_3$ |  | Cl | H | H |
| (OCH$_3$)$_3$ |  | Cl | F | H |
| (OCH$_3$)$_3$ |  | Cl | F | F |
| (OC$_2$H$_5$)$_3$ |  | Cl | H | H |
| (OC$_2$H$_5$)$_3$ |  | Cl | F | H |
| (OC$_2$H$_5$)$_3$ |  | Cl | F | F |
| (OCH$_3$)$_3$ | 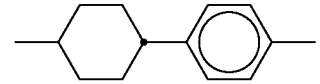 | CH$_3$ | H | H |
| (OC$_2$H$_5$)$_3$ | 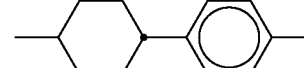 | CH$_3$ | H | H |
| (OCH$_3$)$_3$ | 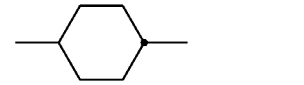 | CH$_3$ | H | H |
| (OC$_2$H$_5$)$_3$ | 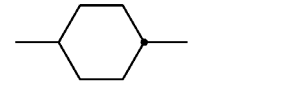 | CH$_3$ | H | H |
| (OCH$_3$)$_3$ | 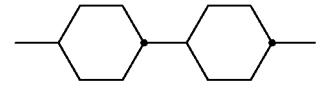 | CH$_3$ | H | H |
| (OC$_2$H$_5$)$_3$ | 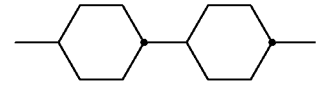 | CH$_3$ | H | H |
| Cl$_3$ | 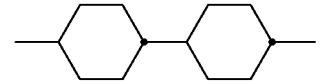 | F | H | H |
| Cl$_3$ | 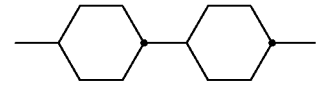 | F | F | H |
| Cl$_3$ | 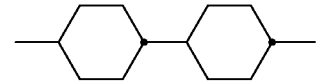 | F | F | F |
| (C$_2$H$_5$)$_3$ | 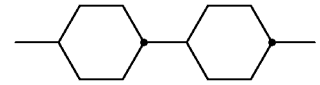 | F | H | H |
| (C$_2$H$_5$)$_3$ | 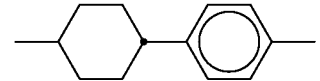 | F | F | H |
| (C$_2$H$_5$)$_3$ | 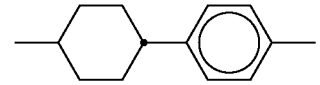 | F | F | F |
| (CH$_3$)$_3$ | 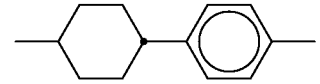 | F | H | H |
| (CH$_3$)$_3$ | | F | F | H |
| (CH$_3$)$_3$ | | F | F | F |
| Cl$_3$ | | F | H | H |

-continued

| $X_aY_bZ_c$ | $-(A^3-Z^2)_n-A^2-Z^1$ | X | Y | Z |
|---|---|---|---|---|
| Cl$_3$ | (cyclohexyl-phenyl) | F | F | H |
| Cl$_3$ | (cyclohexyl-phenyl) | F | F | F |
| (CH$_3$)$_3$ | (cyclohexyl) | F | H | H |
| (CH$_3$)$_3$ | (cyclohexyl) | F | F | H |
| (CH$_3$)$_3$ | (cyclohexyl) | F | F | F |
| (C$_2$H$_5$)$_3$ | (cyclohexyl) | F | H | H |
| (C$_2$H$_5$)$_3$ | (cyclohexyl) | F | F | H |
| (C$_2$H$_5$)$_3$ | (cyclohexyl) | F | F | F |
| Cl$_3$ | (dioxanyl) | F | H | H |
| Cl$_3$ | (dioxanyl) | F | F | H |
| Cl$_3$ | (dioxanyl) | F | F | F |
| (C$_2$H$_5$)$_3$ | (dioxanyl) | F | H | H |
| (C$_2$H$_5$)$_3$ | (dioxanyl) | F | F | H |
| (C$_2$H$_5$)$_3$ | (dioxanyl) | F | F | F |

Example 3

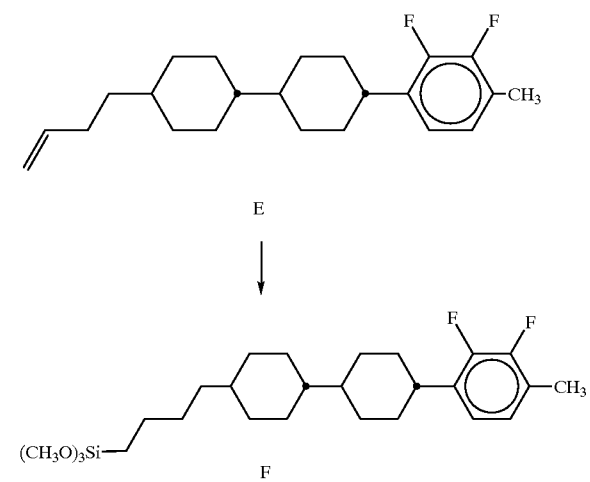

0.014 mol of E are dissolved under a nitrogen atmosphere in 15 ml of dichloromethane, and 0.035 mol of trimethoxysilane is added. 0.1 ml of a 0.03 molar solution of hexachloroplatinic acid in 2-propanol (155 mg of H$_2$PtCl$_6$ in 10 ml of 2-propanol) is added, and the mixture is stirred at room temperature for 4 days and then subjected to customary work-up.

NMR (CDCl$_3$; 300 MHz): δ=2.77 [benzyl-H]; δ=2.27 [CH$_3$]; δ=3.60 [Si(OCH$_3$)$_3$]; δ=6.80 [arom.]

The following compounds of the formula

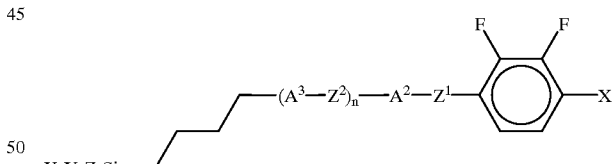

are prepared analogously:

| $X_aY_bZ_c$ | $-(A^3-Z^2)_n-A^2-Z^1-$ | X |
|---|---|---|
| (OCH$_3$)$_3$ | (dicyclohexyl) | OCH$_3$ |
| (OC$_2$H$_5$)$_3$ | (dicyclohexyl) | CH$_3$ |

| $X_aY_bZ_c$ | $-(A^3-Z^2)_n-A^2-Z^1-$ | X |
|---|---|---|
| (OC$_2$H$_5$)$_3$ | 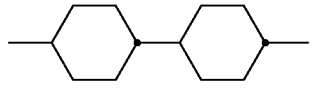 | OCH$_3$ |
| (OCH$_3$)$_3$ | 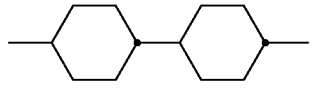 | CH$_3$ |
| (OCH$_3$)$_3$ | 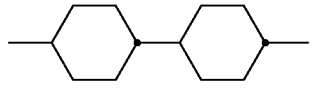 | OCH$_3$ |
| (OC$_2$H$_5$)$_3$ | 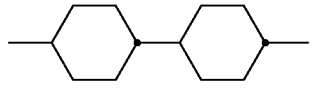 | CH$_3$ |
| (OC$_2$H$_5$)$_3$ | 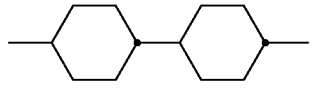 | OCH$_3$ |
| (OCH$_3$)$_3$ | 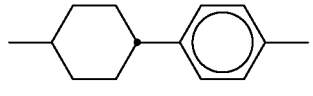 | CH$_3$ |
| (OCH$_3$)$_3$ | 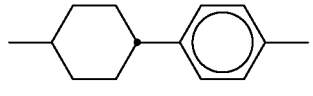 | OCH$_3$ |
| (OC$_2$H$_5$)$_3$ | 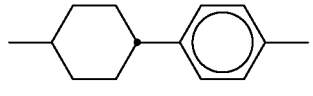 | CH$_3$ |
| (OC$_2$H$_5$)$_3$ | 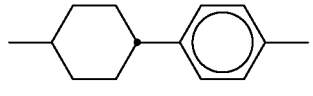 | OCH$_3$ |
| (OCH$_3$)$_3$ | 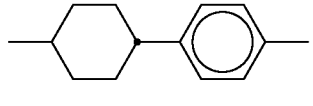 | CH$_3$ |
| (OCH$_3$)$_3$ | 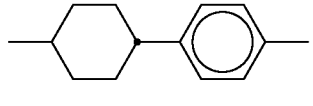 | OCH$_3$ |
| (OC$_2$H$_5$)$_3$ | 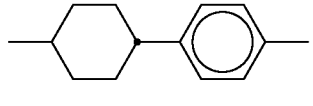 | CH$_3$ |
| (OC$_2$H$_5$)$_3$ | 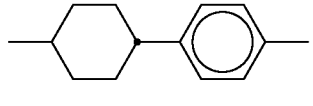 | OCH$_3$ |

| $X_aY_bZ_c$ | $-(A^3-Z^2)_n-A^2-Z^1-$ | X |
|---|---|---|
| (OCH$_3$)$_3$ | 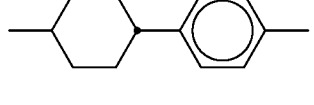 | C$_2$H$_5$ |
| (OCH$_3$)$_3$ |  | OC$_2$H$_5$ |
| (OC$_2$H$_5$)$_3$ | 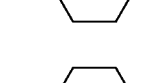 | C$_2$H$_5$ |
| (OC$_2$H$_5$)$_3$ | 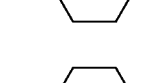 | OC$_2$H$_5$ |
| (OCH$_3$)$_3$ | 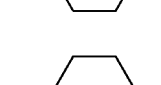 | C$_2$H$_5$ |
| (OCH$_3$)$_3$ | 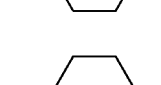 | OC$_2$H$_5$ |
| (OC$_2$H$_5$)$_3$ | 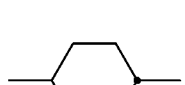 | C$_2$H$_5$ |
| (OC$_2$H$_5$)$_3$ | 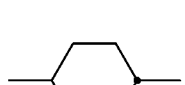 | OC$_2$H$_5$ |
| (OCH$_3$)$_3$ | 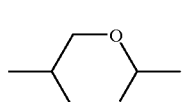 | C$_2$H$_5$ |
| (OCH$_3$)$_3$ | 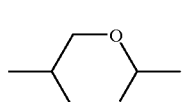 | OC$_2$H$_5$ |
| (OC$_2$H$_5$)$_3$ | 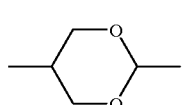 | C$_2$H$_5$ |
| (OC$_2$H$_5$)$_3$ | 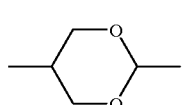 | OC$_2$H$_5$ |
| (OCH$_3$)$_3$ | 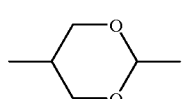 | C$_2$H$_5$ |
| (OCH$_3$)$_3$ | 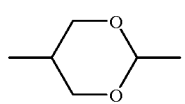 | OC$_2$H$_5$ |

| $X_aY_bZ_c$ | $-(A^3-Z^2)_n-A^2-Z^1-$ | X |
|---|---|---|
| $(OC_2H_5)_3$ | 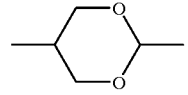 | $C_2H_5$ |
| $(OC_2H_5)_3$ | 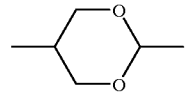 | $OC_2H_5$ |
| $(OCH_3)_3$ | 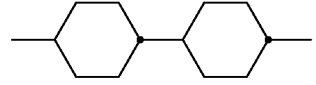 | $n-C_3H_7$ |
| $(OCH_3)_3$ | 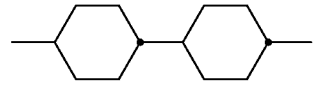 | $OC_3H_7$ |
| $(OC_2H_5)_3$ | 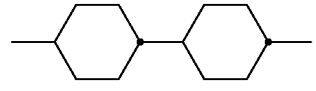 | $n-C_3H_7$ |
| $(OC_2H_5)_3$ | 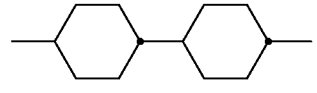 | $OC_3H_7$ |
| $(OCH_3)_3$ | 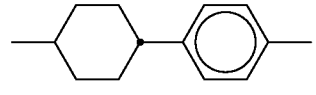 | $n-C_3H_7$ |
| $(OCH_3)_3$ | 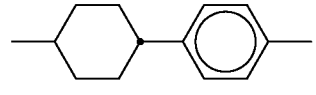 | $OC_3H_7$ |
| $(OC_2H_5)_3$ | 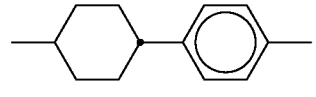 | $n-C_3H_7$ |
| $(OC_2H_5)_3$ | 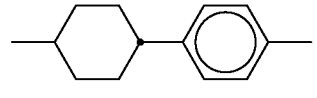 | $OC_3H_7$ |
| $(OCH_3)_3$ | 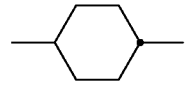 | $n-C_3H_7$ |
| $(OCH_3)_3$ | 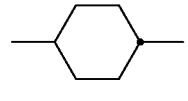 | $OC_3H_7$ |
| $(OC_2H_5)_3$ |  | $n-C_3H_7$ |
| $(OC_2H_5)_3$ |  | $OC_3H_7$ |
| $(OCH_3)_3$ | 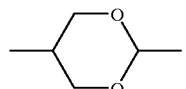 | $n-C_3H_7$ |
| $(OCH_3)_3$ | 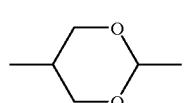 | $OC_3H_7$ |
| $(OC_2H_5)_3$ | 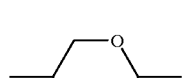 | $n-C_3H_7$ |
| $(OC_2H_5)_3$ | 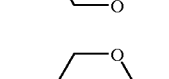 | $OC_3H_7$ |

Example 4

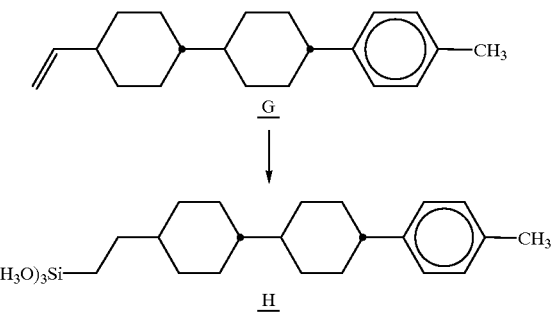

0.018 mol of G are dissolved under a nitrogen atmosphere in 15 ml of dichloromethane, and 0.035 mol of trimethoxysilane is added. 0.1 ml of a 0.03 molar solution of hexachloroplatinic acid in 2-propanol (155 mg of $H_2PtCl_6$ in 10 ml of 2-propanol) is added, and the mixture is stirred at room temperature for 4 hours and then subjected to customary work-up.

NMR (CDCl$_3$; 300 MHz): $\delta$=2.41 [benzyl-H]; $\delta$=2.33 [CH$_3$]; $\delta$=3.60 [Si(OCH$_3$)$_3$]; $\delta$=7.07 [arom.]

The following compounds of the formula $$X_aY_bZ_cSi-\!\!\!\!\!-(A^3-Z^2)_n-A^2-Z^1-\!\!\bigcirc\!\!-X$$

are prepared analogously:

| $X_aY_bZ_c$ | $-(A^3-Z^2)_n-A^2-Z^1-$ | X |
|---|---|---|
| (OCH₃)₃ | cyclohexyl-cyclohexyl | OCH₃ |
| (OC₂H₅)₃ | cyclohexyl-cyclohexyl | CH₃ |
| (OC₂H₅)₃ | cyclohexyl-cyclohexyl | OCH₃ |
| (OCH₃)₃ | cyclohexyl-phenyl | CH₃ |
| (OCH₃)₃ | cyclohexyl-phenyl | OCH₃ |
| (OC₂H₅)₃ | cyclohexyl-phenyl | CH₃ |
| (OC₂H₅)₃ | cyclohexyl-phenyl | OCH₃ |
| (OCH₃)₃ | cyclohexyl | CH₃ |
| (OCH₃)₃ | cyclohexyl | OCH₃ |
| (OC₂H₅)₃ | cyclohexyl | CH₃ |
| (OC₂H₅)₃ | cyclohexyl | OCH₃ |
| (OCH₃)₃ | dioxanyl | CH₃ |
| (OCH₃)₃ | dioxanyl | OCH₃ |

-continued

| $X_aY_bZ_c$ | $-(A^3-Z^2)_n-A^2-Z^1-$ | X |
|---|---|---|
| (OC₂H₅)₃ | dioxanyl | CH₃ |
| (OC₂H₅)₃ | dioxanyl | OCH₃ |
| (OCH₃)₃ | cyclohexyl-cyclohexyl | C₂H₅ |
| (OCH₃)₃ | cyclohexyl-cyclohexyl | OC₂H₅ |
| (OC₂H₅)₃ | cyclohexyl-cyclohexyl | C₂H₅ |
| (OC₂H₅)₃ | cyclohexyl-cyclohexyl | OC₂H₅ |
| (OCH₃)₃ | cyclohexyl-phenyl | C₂H₅ |
| (OCH₃)₃ | cyclohexyl-phenyl | OC₂H₅ |
| (OC₂H₅)₃ | cyclohexyl-phenyl | C₂H₅ |
| (OC₂H₅)₃ | cyclohexyl-phenyl | OC₂H₅ |
| (OCH₃)₃ | cyclohexyl | C₂H₅ |
| (OCH₃)₃ | cyclohexyl | OC₂H₅ |
| (OC₂H₅)₃ | cyclohexyl | C₂H₅ |
| (OC₂H₅)₃ | cyclohexyl | OC₂H₅ |

| $X_aY_bZ_c$ | $-(A^3-Z^2)_n-A^2-Z^1-$ | X |
|---|---|---|
| (OCH₃)₃ | [dioxane ring] | C₂H₅ |
| (OCH₃)₃ | [dioxane ring] | OC₂H₅ |
| (OC₂H₅)₃ | [dioxane ring] | C₂H₅ |
| (OC₂H₅)₃ | [dioxane ring] | OC₂H₅ |
| (OCH₃)₃ | [bicyclohexyl] | n-C₃H₇ |
| (OCH₃)₃ | [bicyclohexyl] | OC₃H₇ |
| (OC₂H₅)₃ | [bicyclohexyl] | n-C₃H₇ |
| (OC₂H₅)₃ | [bicyclohexyl] | OC₃H₇ |
| (OCH₃)₃ | [cyclohexyl-phenyl] | n-C₃H₇ |
| (OCH₃)₃ | [cyclohexyl-phenyl] | OC₃H₇ |
| (OC₂H₅)₃ | [cyclohexyl-phenyl] | n-C₃H₇ |
| (OC₂H₅)₃ | [cyclohexyl-phenyl] | OC₃H₇ |
| (OCH₃)₃ | [cyclohexyl] | n-C₃H₇ |
| (OCH₃)₃ | [cyclohexyl] | OC₃H₇ |
| (OC₂H₅)₃ | [cyclohexyl] | n-C₃H₇ |
| (OC₂H₅)₃ | [cyclohexyl] | OC₃H₇ |
| (OCH₃)₃ | [dioxane ring] | n-C₃H₇ |
| (OCH₃)₃ | [dioxane ring] | OC₃H₇ |
| (OC₂H₅)₃ | [dioxane ring] | n-C₃H₇ |
| (OC₂H₅)₃ | [dioxane ring] | OC₃H₇ |
| Cl₃ | [bicyclohexyl] | OCH₃ |
| Cl₃ | [bicyclohexyl] | OC₂H₅ |
| Cl₃ | [bicyclohexyl] | CH₃ |

Example 5

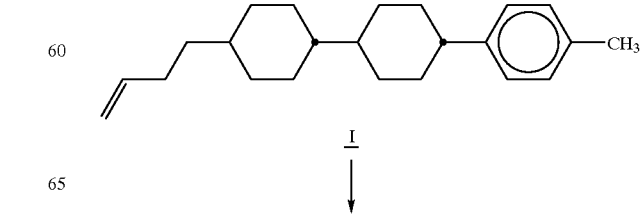

I
↓

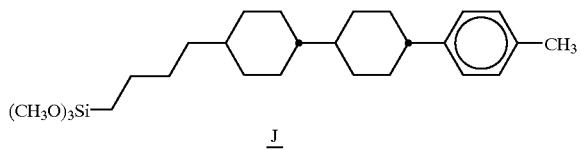

J 0.018 mol of I are dissolved under a nitrogen atmosphere in 15 ml of dichloromethane, and 0.035 mol of trimethoxysilane is added. 0.1 ml of a 0.03 molar solution of hexachloroplatinic acid in 2-propanol (155 mg of $H_2PtCl_6$ in 10 ml of 2-propanol) is added, and the mixture is stirred at room temperature for 4 hours and then subjected to customary work-up.

NMR ($CDCl_3$; 300 MHz): δ=2.43 [benzyl-H]; δ=2.32 [$CH_3$]; δ=3.60 [$Si(OCH_3)_3$]; δ=7.08 [arom.]

The following compounds of the formula

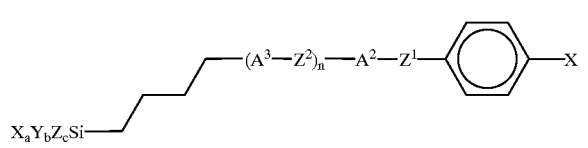

are prepared analogously:

| $X_aY_bZ_c$ | —$(A^3—Z^2)_n$—$A^2$—$Z^1$— | X |
|---|---|---|
| $(OCH_3)_3$ | 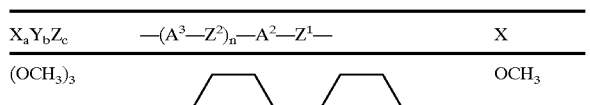 | $OCH_3$ |
| $(OC_2H_5)_3$ | 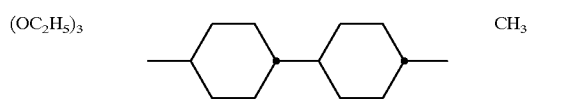 | $CH_3$ |
| $(OC_2H_5)_3$ | 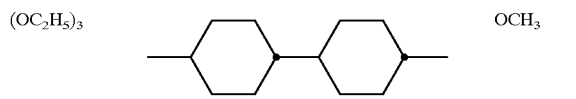 | $OCH_3$ |
| $(OCH_3)_3$ | 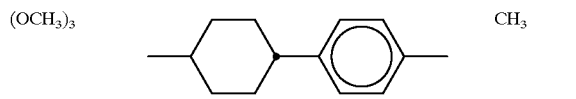 | $CH_3$ |
| $(OCH_3)_3$ | 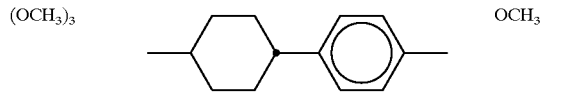 | $OCH_3$ |
| $(OC_2H_5)_3$ | 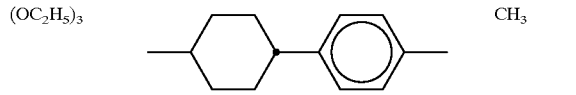 | $CH_3$ |
| $(OC_2H_5)_3$ | 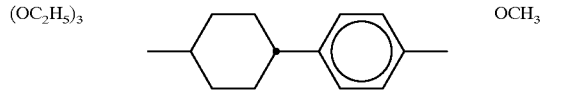 | $OCH_3$ |

| $X_aY_bZ_c$ | —$(A^3—Z^2)_n$—$A^2$—$Z^1$— | X |
|---|---|---|
| $(OCH_3)_3$ | 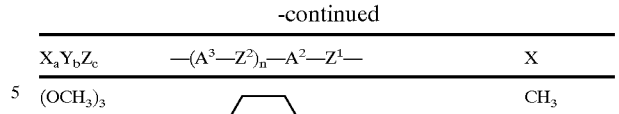 | $CH_3$ |
| $(OCH_3)_3$ | 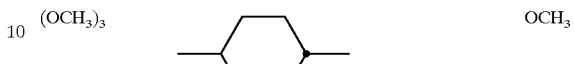 | $OCH_3$ |
| $(OC_2H_5)_3$ |  | $CH_3$ |
| $(OC_2H_5)_3$ | 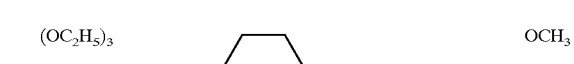 | $OCH_3$ |
| $(OCH_3)_3$ | 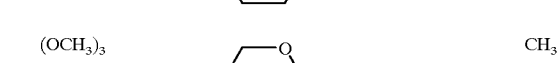 | $CH_3$ |
| $(OCH_3)_3$ | 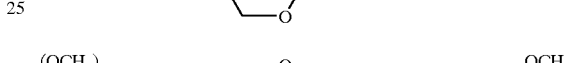 | $OCH_3$ |
| $(OC_2H_5)_3$ | 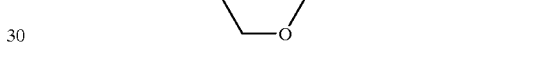 | $CH_3$ |
| $(OC_2H_5)_3$ | 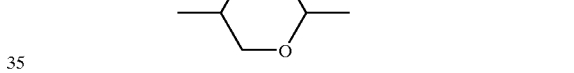 | $OCH_3$ |
| $(OCH_3)_3$ | 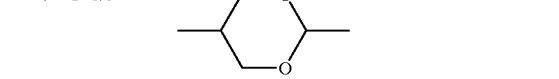 | $C_2H_5$ |
| $(OCH_3)_3$ | 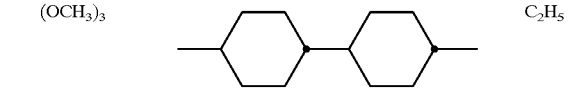 | $OC_2H_5$ |
| $(OC_2H_5)_3$ | 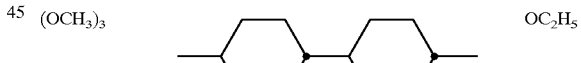 | $C_2H_5$ |
| $(OC_2H_5)_3$ | 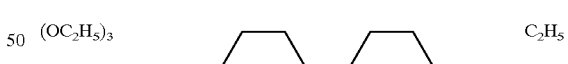 | $OC_2H_5$ |
| $(OCH_3)_3$ | 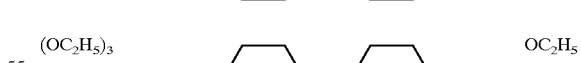 | $C_2H_5$ |
| $(OCH_3)_3$ | 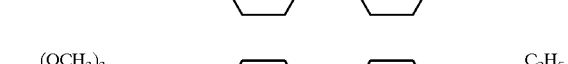 | $OC_2H_5$ |

-continued

| $X_aY_bZ_c$ | —(A³—Z²)ₙ—A²—Z¹— | X |
|---|---|---|
| (OC₂H₅)₃ | cyclohexyl-phenyl | C₂H₅ |
| (OC₂H₅)₃ | cyclohexyl-phenyl | OC₂H₅ |
| (OCH₃)₃ | cyclohexyl | C₂H₅ |
| (OCH₃)₃ | cyclohexyl | OC₂H₅ |
| (OC₂H₅)₃ | cyclohexyl | C₂H₅ |
| (OC₂H₅)₃ | cyclohexyl | OC₂H₅ |
| (OCH₃)₃ | dioxanyl | C₂H₅ |
| (OCH₃)₃ | dioxanyl | OC₂H₅ |
| (OC₂H₅)₃ | dioxanyl | C₂H₅ |
| (OC₂H₅)₃ | dioxanyl | OC₂H₅ |
| (OCH₃)₃ | cyclohexyl-cyclohexyl | n-C₃H₇ |
| (OCH₃)₃ | cyclohexyl-cyclohexyl | OC₃H₇ |
| (OC₂H₅)₃ | cyclohexyl-cyclohexyl | n-C₃H₇ |

-continued

| $X_aY_bZ_c$ | —(A³—Z²)ₙ—A²—Z¹— | X |
|---|---|---|
| (OC₂H₅)₃ | cyclohexyl-cyclohexyl | OC₃H₇ |
| (OCH₃)₃ | cyclohexyl-phenyl | n-C₃H₇ |
| (OCH₃)₃ | cyclohexyl-phenyl | OC₃H₇ |
| (OC₂H₅)₃ | cyclohexyl-phenyl | n-C₃H₇ |
| (OC₂H₅)₃ | cyclohexyl-phenyl | OC₃H₇ |
| (OCH₃)₃ | cyclohexyl | n-C₃H₇ |
| (OCH₃)₃ | cyclohexyl | OC₃H₇ |
| (OC₂H₅)₃ | cyclohexyl | n-C₃H₇ |
| (OC₂H₅)₃ | cyclohexyl | OC₃H₇ |
| (OCH₃)₃ | dioxanyl | n-C₃H₇ |
| (OCH₃)₃ | dioxanyl | OC₃H₇ |
| (OC₂H₅)₃ | dioxanyl | n-C₃H₇ |
| (OC₂H₅)₃ | dioxanyl | OC₃H₇ |
| Cl₃ | cyclohexyl-cyclohexyl | CH₃ |

-continued

| $X_aY_bZ_c$ | $-(A^3-Z^2)_n-A^2-Z^1-$ | X |
|---|---|---|
| Cl₃ | 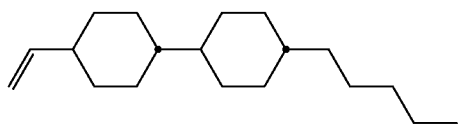 | OCH₃ |
| Cl₃ | | C₂H₅ |
| Cl₃ | | OC₂H₅ |
| Cl₃ | | n-C₃H₇ |
| Cl₃ | | OC₃H₇ |

Example 6

K

↓

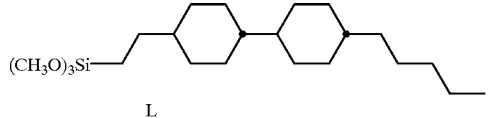

L 0.018 mol of K are dissolved under a nitrogen atmosphere in 15 ml of dichloromethane, and 0.035 mol of trimethoxysilane is added. 0.1 ml of a 0.03 molar solution of hexachloroplatinic acid in 2-propanol (155 mg of H₂PtCl₆ in 10 ml of 2-propanol) is added, and the mixture is stirred at 20° C. overnight and then subjected to customary work-up.

NMR (CDCl₃; 300 MHz): δ=3.57 [Si(OCH₃)₃]

The following compounds of the formula

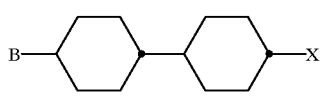

are prepared analogously:

| B | X |
|---|---|
| (OCH₃)₃SiC₂H₄— | CH₃ |
| (OC₂H₅)₃SiC₂H₄— | CH₃ |
| (OCH₃)₃SiC₄H₈— | CH₃ |
| (OC₂H₅)₃SiC₂H₄— | CH₃ |
| Cl₃SiC₂H₄— | CH₃ |
| Cl₃SiC₄H₈— | CH₃ |
| (OCH₃)₃SiC₂H₄— | C₂H₅ |
| (OC₂H₅)₃SiC₂H₄— | C₂H₅ |
| (OCH₃)₃SiC₄H₈— | C₂H₅ |
| (OC₂H₅)₃SiC₂H₄— | C₂H₅ |
| Cl₃SiC₂H₄— | C₂H₅ |
| Cl₃SiC₄H₈— | C₂H₅ |
| (OCH₃)₃SiC₂H₄— | n-C₃H₇ |
| (OC₂H₅)₃SiC₂H₄— | n-C₃H₇ |
| (OCH₃)₃SiC₄H₈— | n-C₃H₇ |
| (OC₂H₅)₃SiC₂H₄— | n-C₃H₇ |
| Cl₃SiC₂H₄— | n-C₃H₇ |
| Cl₃SiC₄H₈— | n-C₃H₇ |
| (OCH₃)₃SiC₂H₄— | n-C₄H₉ |
| (OC₂H₅)₃SiC₂H₄— | n-C₄H₉ |
| (OCH₃)₃SiC₄H₈— | n-C₄H₉ |
| (OC₂H₅)₃SiC₂H₄— | n-C₄H₉ |
| Cl₃SiC₂H₄— | n-C₄H₉ |
| Cl₃SiC₄H₈— | n-C₄H₉ |
| (OCH₃)₃SiC₂H₄— | n-C₅H₁₁ |
| (OC₂H₅)₃SiC₂H₄— | n-C₅H₁₁ |
| (OCH₃)₃SiC₄H₈— | n-C₅H₁₁ |
| (OC₂H₅)₃SiC₂H₄— | n-C₅H₁₁ |
| Cl₃SiC₂H₄— | n-C₅H₁₁ |
| Cl₃SiC₄H₈— | n-C₅H₁₁ |
| (OCH₃)₃SiC₂H₄— | n-C₆H₁₃ |
| (OC₂H₅)₃SiC₂H₄— | n-C₆H₁₃ |
| (OCH₃)₃SiC₄H₈— | n-C₆H₁₃ |
| (OC₂H₅)₃SiC₂H₄— | n-C₆H₁₃ |
| Cl₃SiC₂H₄— | n-C₆H₁₃ |
| Cl₃SiC₄H₈— | n-C₆H₁₃ |

Use Example 1

Coating of Glass Surfaces 0.2 g of the compound

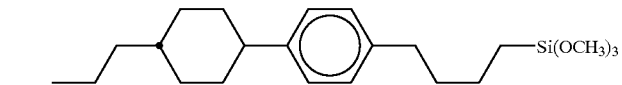

are mixed homogeneously in a binder consisting of 4 g of PVP K-30 (GAF) and 16 g of ethanol, with stirring using a propeller stirrer. The viscosity of the visually clear solution is 40 seconds (DIN 4 mm flow cup).

The resultant printing medium is applied to ITO glasses using 6 μm, 12 μm and 24 μm spiral doctor blades.

The coated substrates are dried at 140° C. for 30 minutes. The substrates are then treated for 2 minutes in an ultrasound bath containing a solution of demineralized water/ethanol 1:1 in order to remove the auxiliaries.

The coated areas of the ITO glasses exhibit the desired alignment in the test, while the uncoated areas do not exhibit this, as expected.

The entire disclosure of all applications, patents and publications, cited above, and of corresponding German application No. 197 48 808.0, filed Nov. 5, 1997 is hereby incorporated by reference.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. Compounds of the formulae I1 to I3

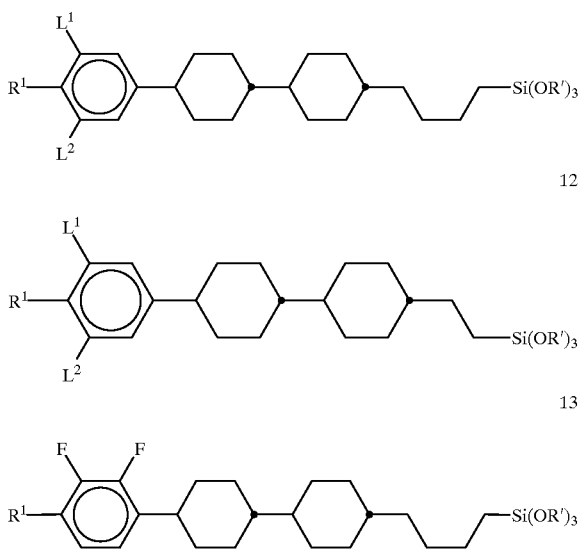

in which

L¹ and L² are each, independently of one another, H or F,

R¹ is a chiral or achiral alkyl group having up to 10 carbon atoms, in which, in addition, one or two non-adjacent CH₂ groups may be replaced by —O— atoms, or is F, Cl or a halogenated alkyl, alkoxy, alkenyl or alkenyloxy radical having 1 to 3 carbon atoms R¹ is an alkyl group having 1 to 15 carbon atoms, in which, in addition, one or more non-adjacent CH₂ groups may be replaced by —O—, —CO— and/or —CH=CH—.

2. A method of using a compound according to claim 1 which comprises incorporating a compound of claim 3 as a component of liquid crystalline dielectrics for electro-optical display elements.

3. Liquid crystalline dielectric for electro-optical display elements having at least two liquid crystal components, characterized in that at least one compound is a compound of formulae I1 to I3 according to claim 1.

4. Electro-optical display element, characterized in that it contains a dielectric according to claim 3.

5. A method of using the compounds of the formula I

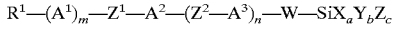

for producing homeotropic alignment of liquid-crystalline phases on surfaces which comprises coating the surfaces with compounds of formula I
in which R¹ is a chiral or achiral alkyl group having up to 10 carbon atoms, in which, in addition, one or two non-adjacent CH₂ groups may be replaced by —O— atoms, or is F, Cl or a halogenated alkyl, alkoxy, alkenyl or alkenyloxy radical having 1 to 3 carbon atoms A¹, A² and A³ are each, independently of one another, a) a 1,4-cyclohexylene radical, in which, in addition, one or two non-adjacent CH₂ groups may be replaced by —O— and/or —S—,
b) a 1,4-cyclohexenylene radical, or
c) a 1,4-phenylene radical, in which, in addition, one or more CH groups may be replaced by N atoms,
where the radicals a), b) and c) may be substituted by one or two fluorine atoms, Z¹ and Z² are each, independently of one another, —CH₂CH₂—, —CO—O—, —(C₂H₄)—, —(CH₂)₄——CH₂CH=CHCH₂—, —CH₂—O—, —O—CH₂—, —CH=CH—, —C≡C— or a single bond, m is 0 or 1, n is 0, 1 or 2 where m+n is ≧1, W is a straight-chain or branched alkylene group having up to 10 carbon atoms, in which, in addition, one or two non-adjacent CH₂ groups may be replaced by —CHF— and/or —CH(CF₃)—, X, Y and Z are each, independently of one another, OCN, CN, R', OR', H or Cl, where at least one of the substituents X, Y and Z is not H, R' is an alkyl group having 1 to 15 carbon atoms, in which, in addition, one or more non-adjacent CH₂ groups may be replaced by —O—, —CO— and/or —CH=CH—, and a, b and c are 0, 1, 2 or 3, where a+b+c=3.

6. A method as in claim 5 wherein the compounds of the formula I are used in a printing process for producing homeotropic alignment of liquid-crystalline phases on surfaces which comprises coating the surfaces with compounds of formula I in a printing process.

7. A method as in claim 6 wherein the compounds of formula I which are used are selected from those of formula I wherein m=1 and n=0.

8. A method as in claim 7 wherein the compounds of formula I which are used are selected from those of formula I wherein m=1, n=0 and Z¹ is a single bond.

9. A method as in claim 5 wherein the compounds of formula I which are used are selected from those of the formulae I1, I2, I3 or I4

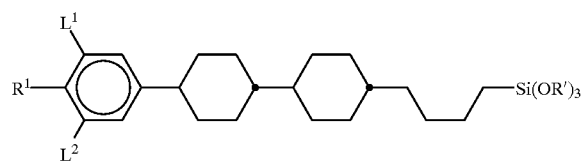

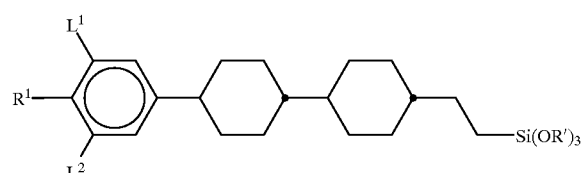

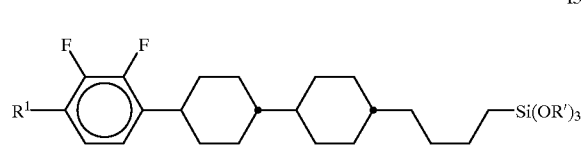

I4

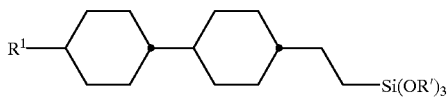

in which

L$^1$ and L$^2$ are each independently of one another, H or F, and

R$^1$ is a chiral or achiral alkyl group having up to 10 carbon atoms, in which, in addition, one or two non-adjacent CH$_2$ groups may be replaced by —O— atoms, or is F, Cl or a halogenated alkyl, alkoxy, alkenyl or alkenyloxy radical having 1 to 3 carbon atoms R' is an alkyl group having 1 to 15 carbon atoms, in which, in addition, one or more non-adjacent CH$_2$ groups may be replaced by —O—, —CO— and/or —CH=CH—.

10. A method of using compounds of formula I

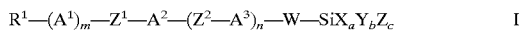

for the preparation of liquid-crystalline pigments by three-dimensional crosslinking of the silanols prepared from compounds of the formula I, which comprises applying the silanols in the liquid state to a smooth substrate, hardening the silanol film formed, and commuting the film to give platelet-like pigments, in which R$^1$ is a chiral or achiral alkyl group having up to 10 carbon atoms, in which, in addition, one or two non-adjacent CH$_2$ groups may be replaced by —O— atoms, or is F, Cl or a halogenated alkyl, alkoxy, alkenyl or alkenyloxy radical having 1 to 3 carbon atoms A$^1$, A$^2$ $^{and\ A3}$ are each, independently of one another,
  a) a 1,4-cyclohexylene radical, in which, in addition, one or two non-adjacent CH$_2$ groups may be replaced by —O— and/or —S—,
  b) a 1,4-cyclohexenylene radical, or
  c) a 1,4-phenylene radical, in which, in addition, one or more CH groups may be replaced by N atoms,
  where the radicals a), b) and c) may be substituted by one or two fluorine atoms, Z$^1$ and Z$^2$ are each, independently of one another, —CH$_2$CH$_2$—, —CO—O—, —(C$_2$H$_4$)—, —(CH$_2$)$_4$— —CH$_2$CH=CHCH$_2$—, —CH$_2$—O—, —O—CH$_2$—, —CH=CH—, —C≡C—, or a single bond, m is 0 or 1, n is 0, 1 or 2 where m+n is ≧1, W is a straight-chain or branched alkylene group having up to 10 carbon atoms, in which, in addition, one or two non-adjacent CH$_2$ groups may be replaced by —CHF— and/or —CH(CF$_3$)—, X, Y and Z are each, independently of one another, OCN, CN, R', OR', H or Cl, where at least one of the substituents X, Y and Z is not H, R' is an alkyl group having 1 to 15 carbon atoms, in which, in addition, one or more non-adjacent CH$_2$ groups may be replaced by —O—, —CO—, and/or —CH=CH—, and a, b and c are 0, 1, 2 or 3, where a+b+c=3.

* * * * *

UNITED STATES PATENT AND TRADEMARK OFFICE
CERTIFICATE OF CORRECTION

PATENT NO.    : 6,287,650 B1
DATED         : September 11, 2001
INVENTOR(S)   : Pauluth et al.

It is certified that error appears in the above-identified patent and that said Letters Patent is hereby corrected as shown below:

<u>Column 43,</u>
Line 67, reads "A1, $A^{2 \; and \; A3}$" should read -- A1, A2, and A3 --

<u>Column 44,</u>
Line 11, reads "$-(CH_2)$" should be -- $-(CH_2)_4$, --
Line 12, delete "$_4$—"
Line 34, reads "as in claim 6" should read -- as in claim 5 --

<u>Column 46,</u>
Line 3, reads "A1, $A^{2 \; and \; A3}$" should read -- $A^1$, $A^2$, and $A^3$ --
Line 13, reads "$-(CH_2)_4-$" should read -- $-(CH_2)_4-$, --

Signed and Sealed this

Twenty-fourth Day of December, 2002

JAMES E. ROGAN
*Director of the United States Patent and Trademark Office*